United States Patent
Ungashe et al.

(10) Patent No.: US 12,180,220 B2
(45) Date of Patent: *Dec. 31, 2024

(54) HETEROARYL MODULATORS OF RAS GTPase

(71) Applicant: Tosk, Inc., Mountain View, CA (US)

(72) Inventors: Solomon B. Ungashe, Mountain View, CA (US); Stephen D. Yanofsky, Mountain View, CA (US)

(73) Assignee: Tosk, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/484,739

(22) Filed: Sep. 24, 2021

(65) Prior Publication Data
US 2022/0112205 A1    Apr. 14, 2022

Related U.S. Application Data

(60) Provisional application No. 63/091,450, filed on Oct. 14, 2020.

(51) Int. Cl.
| | | |
|---|---|---|
| C07D 491/056 | (2006.01) | |
| C07D 239/84 | (2006.01) | |
| C07D 401/12 | (2006.01) | |
| C07D 401/14 | (2006.01) | |
| C07D 405/10 | (2006.01) | |
| C07D 405/14 | (2006.01) | |
| C07D 471/04 | (2006.01) | |
| C07D 519/00 | (2006.01) | |
| C12N 9/99 | (2006.01) | |

(52) U.S. Cl.
CPC ....... C07D 491/056 (2013.01); C07D 239/84 (2013.01); C07D 401/12 (2013.01); C07D 401/14 (2013.01); C07D 405/10 (2013.01); C07D 405/14 (2013.01); C07D 471/04 (2013.01); C07D 519/00 (2013.01); C12N 9/99 (2013.01)

(58) Field of Classification Search
CPC .......................... C07D 491/056; C07D 239/84; C07D 401/12; C07D 401/14; C07D 405/10; C07D 405/14; C07D 471/04; C07D 519/00
See application file for complete search history.

(56) References Cited

U.S. PATENT DOCUMENTS

| | | | |
|---|---|---|---|
| 7,691,866 B2 * | 4/2010 | Ramurthy | A61P 15/00 514/266.4 |
| 8,202,883 B2 | 6/2012 | Gerlach et al. | |
| 10,344,033 B2 * | 7/2019 | Boyle | C07D 487/04 |
| 2018/0086752 A1 | 3/2018 | Rabizadeh et al. | |
| 2018/0099957 A1 | 4/2018 | Ma et al. | |
| 2018/0155348 A1 | 6/2018 | Li et al. | |
| 2019/0022074 A1 | 1/2019 | Hadari et al. | |
| 2019/0134056 A1 | 5/2019 | Tolias et al. | |
| 2020/0199081 A1 | 6/2020 | Cui et al. | |
| 2022/0073498 A1 | 3/2022 | Iliopoulos et al. | |
| 2022/0227740 A1 * | 7/2022 | Ungashe | C07D 413/14 |

FOREIGN PATENT DOCUMENTS

| | | |
|---|---|---|
| KR | 10-2011-0114663 A | 10/2011 |
| WO | WO0202563 A2 | 1/2002 |
| WO | WO2005012256 A1 | 2/2005 |
| WO | WO2017023133 A2 | 2/2017 |
| WO | WO2020127200 A1 | 6/2020 |
| WO | WO2020132071 A1 | 6/2020 |
| WO | WO2020180768 A1 | 9/2020 |
| WO | WO2020180770 A1 | 9/2020 |
| WO | WO 2020/214537 A1 * | 10/2020 |

OTHER PUBLICATIONS

Britten, Carolyn D, Cancer Chemother Pharmacol (2013) 71: 1395-1409.*
Qiu et al., J Cell Mol Med. 2019; 23;7632-7640.*
McCarthy et al., Discovery of High-Affinity Noncovalent Allosteric KRAS Inhibitors That Disrupt Effector Binding, ACS Omega, 2019, vol. 4, p. 2921-2930.
Chemical Abstract compounds, STN express RN 1269064-16-5 (Entered STN: Mar. 21, 2011).
Chemical Abstract compounds, STN express RN 2109536-59-4 (Entered STN: Aug. 7, 2017).
Chemical Abstract compounds, STN express RN 1360253-07-1 (Entered STN: Mar. 7, 2012).
Kaswan et al., Synthesis of 5,7-diarylpyrazolo [1,5-a] pyrimidines via KOH mediated tandem reaction of 1H-pyrazol-3-amines and chalcones, Tetrahedron Letters, 2015, vol. 56, No. 3, pp. 549-553.
Compton et al., Pyrazolo [1,5-a] pyrimidines: estrogen receptor ligands possessing estrogen receptor β antagonist activity, J. Med. Chem., 2004, vol. 47, No. 24, pp. 5872-5893.
Quiroga et al., Regioselective formylation of pyrazolo [3,4-b] pyridine and pyrazolo [1,5-a] pyrimidine systems using Vilsmeier-Haack conditions, Tetrahedron Letters, 2008, vol. 49, No. 17, pp. 2689-2691.

(Continued)

*Primary Examiner* — Rebecca L Anderson
(74) *Attorney, Agent, or Firm* — Todd Esker; Michael J. Blessent; Bret E. Field

(57) ABSTRACT

RAS modulating compounds and methods of using the same are provided. The compounds find use in modulating the activity of a target RAS in a sample. The target RAS can be a mutant RAS that is implicated in a disease of interest. In some cases, the subject compounds can inhibit the growth of cancer cells whose progression is driven by kRAS or a mutated kRAS. Methods of treating a subject for a RAS driven disease including administering a therapeutically effective amount of the subject compound are provided. Also provided are pharmaceutical compositions and kits which include the subject compounds.

13 Claims, No Drawings

(56) References Cited

OTHER PUBLICATIONS

Kettle et al., Covalent inhibitors of the GTPase KRAS G12C: A review of the patent literature, Expert Opinion on Therapeutic Patents, Jan. 2020, vol. 30, No. 2, p. 103-120.
Zeng et al., Potent and selective covalent quinazoline inhibitors of KRAS G12C, Cell Chemical Biology, Aug. 2017, vol. 24, p. 1005-1016.
Lu et al., KRAS G12C drug development: Discrimination between Switch II pocket configurations using hydrogen/deuterium-exchange mass spectrometry, Structure, Sep. 2017, vol. 25, p. 1442-1448.
Britten, PI3K and MEK inhibitor combinations: examining the evidence in selected tumor types, Cancer Chemother Pharmacol, Feb. 2013, vol. 71, p. 1395-1409.
Friess et al., Pancreatic cancer: the potential clinical relevance of alterations in growth factors and their receptors, J Mol Med, 1996, vol. 74, p. 35-42.
Bailey et al., FXR silencing in human colon cancer by DNA methylation and KRAS signaling, Am J Physiol Gastrointest Liver Physiol, 2014, vol. 306, p. G48-G58.
Mathison et al., Abstract 1391: The epigenetic regulator, G9a, is a KRAS-inducible protein and its inactivation inhibits PanIN formation by this oncogene, Cancer Res, Jul. 2017, vol. 77, Supp. 13, No. 1391.

* cited by examiner

HETEROARYL MODULATORS OF RAS GTPase

CROSS-REFERENCE TO RELATED APPLICATION

Pursuant to 35 U.S.C. § 119(e), this application claims priority to the filing date of U.S. Provisional Patent Application Ser. No. 63/091,450 filed Oct. 14, 2020; the disclosure of which application is herein incorporated by reference.

GOVERNMENT RIGHTS

This invention was made with government support under grant No. R44CA189549, awarded by the Department of Health and Human Services. The government has certain rights in the invention.

INTRODUCTION

The RAS family of proteins represents a group of 189 amino acid (21 kDa molecular mass), closely related, monomeric, globular GTPases which associate with the plasma membrane and bind either guanosine diphosphate (GDP) or guanosine triphosphate (GTP). The proteins act as molecular switches in signal transduction in cells. When bound to GDP, RAS is in its off (resting) position and is inactive. When activated by its cell surface growth factor EGF, RAS exchanges bound GDP for GTP. With GTP bound, RAS is "switched on" and can interact with and activate other proteins including its "downstream targets," such as the pro-growth Ras-Raf-MEK-ERK pathway. The RAS protein itself has a very low intrinsic ability to turn itself off by hydrolyzing GTP back to GDP. Switching RAS off requires extrinsic proteins termed GTPase-activating proteins (GAPs) that interact with RAS and greatly accelerate the conversion of GTP to GDP. Any mutation in RAS which affects its ability to interact with a GAP or to convert GTP back to GDP can result in a prolonged activation of the protein and consequently provide a prolonged signal to cells to proliferate. Because these signals result in cell growth and division, overactive RAS signaling can lead to cancer. Conversely, compounds that bind the inactive GDP-bound RAS and inhibit the exchange of GDP for GTP inhibit RAS activity by preventing its association with, and activation of, its downstream targets. Compounds that inhibit the association of activated GTP-bound RAS with its downstream targets such as the RAF family of proteins also inhibit RAS-induced promotion of cell growth and proliferation and are of interest as potential anti-cancer drugs.

Mutations in any one of the three main isoforms of RAS (hRAS, nRAS, or kRAS) genes are among the most common events in human tumorigenesis. Remarkably, RAS mutations are detected in 30% of tumors and of these mutations 86% are in kRAS. By comparison, the rates of oncogenic mutation occurring in the nRAS and hRAS family members are much lower (11% and 3% respectively). The most common kRAS mutations are at residue G12 and G13 in the P-loop and at residue Q61. kRAS is mutated in 61% of pancreatic cancers, 43% of colon cancers, 21% of endometrial cancers, 26% of lung adenocarcinomas, e.g., non-small cell lung carcinoma, 3% of skin cancers, 4% of acute myeloid leukemia (AML) liquid tumors and in 1% or so of multiple myeloma cancers.

SUMMARY

RAS modulating compounds and methods of using the same are provided. The subject compounds comprise a core fused bicyclic group based on a quinoline-type scaffold having two fused six-membered aryl or heteroaryl rings, where one or more aromatic carbon atoms of the rings is substituted with a fused bicyclic pyridyl motif. The core fused bicyclic group may be linked to a cyclic group (A) through the 2-position via a linker. The linked cyclic group can be optionally substituted with an amido or a carbamate group. The compounds find use in modulating the activity of a target RAS in a sample. The target RAS can be a mutant RAS that is implicated in a disease of interest. In some cases, the subject compounds can inhibit the growth of cancer cells whose progression is driven by kRAS or a mutated kRAS. Methods of treating a subject for a RAS driven disease including administering a therapeutically effective amount of the subject compound are provided. Also provided are pharmaceutical compositions and kits which include the subject compounds.

Definitions

Unless defined otherwise, all technical and scientific terms used herein have the same meaning as is commonly understood by one of skill in the art to which this invention belongs. All patents and publications referred to herein are incorporated by reference. As used in the specification and claims, the singular form "a", "an" and "the" include plural references unless the context clearly dictates otherwise.

$IC_{50}$ is half maximal inhibitory concentration and a measure of potency of the given compound against KRAS.

RLU is relative luminescence unit measuring the level of ATP in cell proliferation assays.

Alkyl by itself or as part of another substituent refers to a monovalent saturated aliphatic hydrocarbon group. This term includes linear, cyclic, or branched groups or a combination thereof. The group can have the number of carbon atoms designated (e.g., C1-C8 means one to eight carbon atoms). In some cases, an alkyl group has from 1 to 10 carbon atoms, such as 1 to 6 carbon atoms, or 1 to 5, or 1 to 4, or 1 to 3 carbon atoms. Examples of alkyl groups include, but are not limited to, methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc.

Structures for a few exemplary alkyl groups are provided in the Table I below.

TABLE I

| Structure of exemplary alkyl groups |
|---|
| —CH₃ |
| Methyl |
| CH₃—CH₂ |
| Ethyl |
| CH₃—CH₂—CH₂ |
| Propyl |

TABLE I-continued

Structure of exemplary alkyl groups

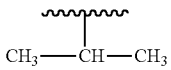

Isopropyl

Butyl

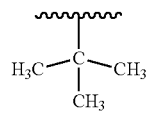

tert-Butyl

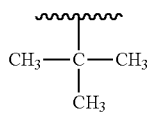

sec-Butyl

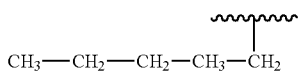

Pentyl

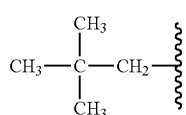

Neopentyl

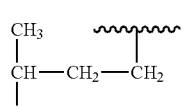

Isopentyl

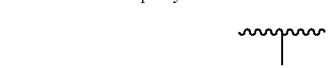

Hexyl

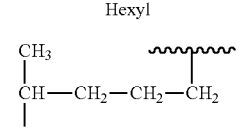

Isohexyl

Alkyl groups can be substituted or unsubstituted, unless otherwise indicated.

The term "substituted alkyl" refers to an alkyl group as defined herein wherein one or more carbon atoms in the alkyl chain have been optionally replaced with a heteroatom such as O—, N—, S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO2-alkyl, —SO2-aryl, SO2-heteroaryl, and —NRaRb, wherein R' and R" may be the same or different and are chosen from hydrogen, optionally substituted alkyl, cycloalkyl, alkenyl, cycloalkenyl, alkynyl, aryl, heteroaryl and heterocyclic. Examples of substituted alkyl include haloalkyl, thioalkyl, aminoalkyl, and the like.

Alkenyl refers to an unsaturated hydrocarbon group which may be linear, cyclic or branched or a combination thereof. Alkenyl groups with 2-8 carbon atoms are preferred. The alkenyl group may contain 1, 2 or 3 carbon-carbon double bonds. Examples of alkenyl groups include ethenyl, n-propenyl, isopropenyl, n-but-2-enyl, n-hex-3-enyl, cyclohexenyl, cyclopentenyl and the like. Alkenyl groups can be substituted or unsubstituted, unless otherwise indicated.

Aryl or Ar refers to a polyunsaturated, aromatic hydrocarbon group having a single ring (bicyclic) or multiple rings (preferably bicyclic) which can be fused together or linked covalently. In some cases, an Aryl group has 6 to 18 carbon atoms, such as 6-10 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. Examples of aryl groups include, but are not limited to, phenyl and naphthalene-1-yl, naphthalene-2-yl, biphenyl and the like. Aryl groups can be substituted or unsubstituted, unless otherwise indicated. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO— heteroaryl, —SO$_2$-alkyl, —SO$_2$-substituted alkyl, —SO$_2$-aryl, —SO$_2$-heteroaryl and trihalomethyl. The structures of a few exemplary aryl groups are provided in Table II below.

TABLE II

Examples of aryl groups

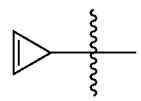 [SMILES: *C1C=C1]

Cyclopropenyl

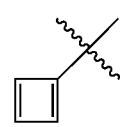 [SMILES: *C1=CC=C1]

TABLE II-continued

Examples of aryl groups

Cyclobuta-1,3-dienyl

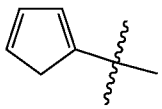 [SMILES: *C1=CC=CC1]

Cyclopenta-1,3-dienyl

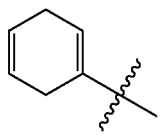 [SMILES: *C1=CCC=CC1]

Cyclohexa-1,4-dienyl

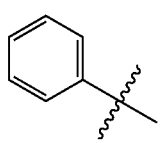 [SMILES: *c1ccccc1]

Benzyl

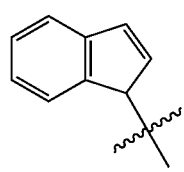 [SMILES: *C1C=Cc2ccccc21]

1H-indenyl

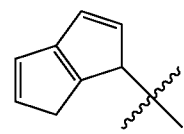 [SMILES: *C1C=CC2=C1CC=C2]

1,6-dihydropentalenyl

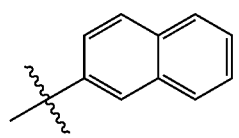 [SMILES: *c1ccc2ccccc2c1]

Napthylenyl

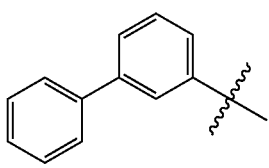 [SMILES: *c1cccc(-c2ccccc2)c1]

1,1'-Biphenyl

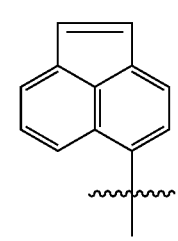 [SMILES: *c1ccc2c3c(cccc13)C=C2]

TABLE II-continued

Examples of aryl groups

Acenaphthylenyl

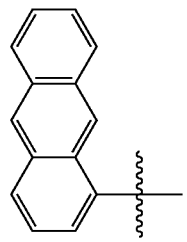 [SMILES: *c1cccc2cc3ccccc3cc12]

Anthracenyl

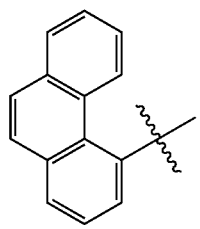 [SMILES: *c1cccc2ccc3ccccc3c12]

Phenanthrenyl

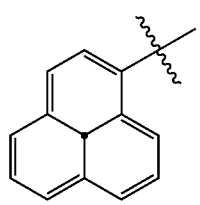

$3a^1$H-phenalenyl

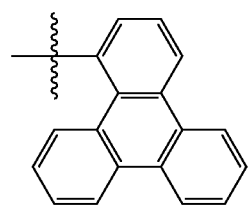 [SMILES: *c1cccc2c3ccccc3c3ccccc3c12]

Triphenylenyl

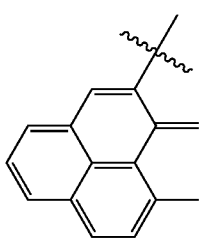 [SMILES: *c1cc2cccc3ccc(C)c(c1=C)c32]

Pyrenyl

DIRAS is diverse RAS, which is a distinct branch of the functionally diverse RAS superfamily of monomeric GTPases.

DMEM is Dulbecco's Modified Eagle Medium. It is a modification of Basal Medium Eagle (BME) that contains a four-fold higher concentration of amino acids and vitamins, as well as additional supplementary components. The original DMEM formula contains 1000 mg/L of glucose and was first reported for culturing embryonic mouse cells.

Effective amount or therapeutically effective amount refers to an amount of a compound sufficient to effect the intended application, such as an amount sufficient to treat a specified disorder or disease or one or more of its symptoms and/or to prevent the occurrence of the disease or disorder. The therapeutically effective amount may vary depending upon the intended treatment application (e.g., in vivo), or the subject and disease condition being treated, e.g., the weight and age of the subject, the severity of the disease condition, the manner of administration and the like, which can readily be determined by one of ordinary skill in the art.

Enantiomer. Enantiomers are stereoisomers that are non-superimposable mirror images. A molecule with 1 chiral carbon atom exists as 2 stereoisomers termed enantiomers. Enantiomers differ in their configuration (R or S) at the stereogenic center.

ERAS is RAS expressed by ES cells. This is a constitutively active member of the small GTPase RAS protein family. The encoded protein activates the phosphatidylinositol 3-kinase signal transduction pathway in undifferentiated stem cells but is not expressed in differentiated cells. This gene may be involved in cancer and chemotherapy resistance.

ERK is widely expressed extracellular-signal-regulated protein kinase and intracellular signaling molecules involved in functions including the regulation in differentiated cells of meiosis, mitosis, and post-mitotic action.

GEM is GTP binding protein overexpressed in skeletal muscle. The protein belongs to the RAD/GEM family of GTP-binding proteins. It is associated with the inner face of the plasma membrane and could play a role as a regulatory protein in receptor-mediated signal transduction. Alternative splicing occurs at this locus and two transcript variants encoding the same protein have been identified.

G Domain is a highly conserved domain common to all GTPases that is located on the largest of the G proteins three subunits, the α unit. The two smaller subunits are the β and γ units.

GTPase refers to a large family of hydrolase enzymes that bind and hydrolyze GTP.

Halo or halogen, by itself or as part of a substituent refers to a chlorine, bromine, iodine, or fluorine atom. Additionally, "haloalkyl", as a substituted alkyl group, refers to a monohaloalkyl or polyhaloalkyl group, most typically substituted with from 1-3 halogen atoms. Examples include, but are not limited to, 1-chloroethyl, 3-bromopropyl, trifluoromethyl and the like.

Heterocyclyl refers to a saturated or unsaturated non-aromatic group containing at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like. Heterocyclic groups can be monocyclic or can be fused or linked covalently to an aryl or heteroaryl ring system.

Heteroaryl refers to an aromatic group containing at least one heteroatom. Examples include, but are not limited to, pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl. Preferred heteroaryl groups are those having at least one aryl ring nitrogen atom, such as quinolinyl, quinoxalinyl, purinyl, benzimidazolyl, benzopyrazolyl, benzotriazolyl, benzothiazolyl, indolyl, quinolyl, isoquinolyl and the like. Preferred 6-ring heteroaryl systems include pyridyl, pyridazinyl, pyrazinyl, pyrimidinyl, triazinyl and the like. Preferred 5-ring heteroaryl systems include isothiazolyl, pyrazolyl, imidazolyl, thienyl, furyl, triazolyl, tetrazolyl, oxazolyl, isoxazolyl, oxadiazolyl, thiadiazolyl, pyrrolyl, thiazolyl and the like.

Heterocyclyl and heteroaryl groups can be attached at any available ring carbon or heteroatom. Each heterocyclyl and heteroaryl may have one or more rings. When multiple rings are present, they can be fused together or linked covalently. Each heterocyclyl and heteroaryl must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Heterocyclyl and heteroaryl groups can be substituted or unsubstituted, unless otherwise indicated. For substituted groups, the substitution may be on a carbon or heteroatom. The structures of a few exemplary heterocyclyls are shown in Table III below.

TABLE III

Examples of heterocyclyls

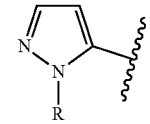

Substituted Pyrazolyl

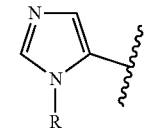

Substituted Imidazole

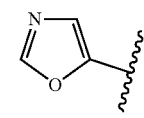 [SMILES: *c1cnco1]

Oxazolyl

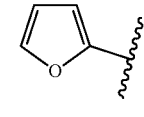 [SMILES: *c1ccco1]

Furanyl

TABLE III-continued

Examples of heterocyclyls

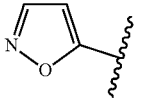

Isoxazolyl

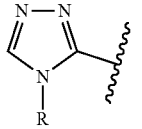

Substituted 1,2,4 Triazolyl

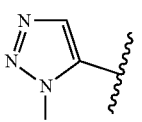

Substituted 1,2,3 Triazolyl

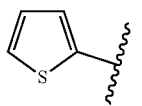 [SMILES: *c1cccs1]

Thiophenyl

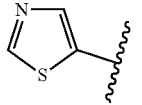 [SMILES: *c1cncs1]

Thiazolyl

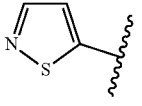 [SMILES: *c1ccns1]

Isothiazolyl

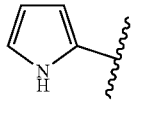

Pyrrolyl

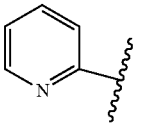 [SMILES: *c1ccccn1]

Pyridinyl

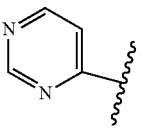 [SMILES: *c1ccncn1]

Pyrimidinyl

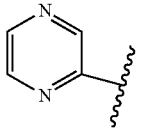 [SMILES: *c1cnccn1]

Pyrazinyl

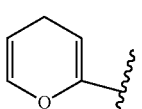

Pyranyl

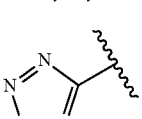

Tetrazolyl

Substituents of interest for substituted alkyl, substituted alkenyl, and substituted alkynyl groups include, but are not limited to, halogen, —CN, —CO$_2$R', —C(O)R', —C(O)NR'R", oxo (=O), —OR', —OC(O)R', —OC(O)NR'R"— NO$_2$, —NR'C(O)R', —NR'"C(O)NR'R", —NR'R", —NR'CO$_2$R", —NR'S(O)$_2$R'", —SR', —S(O)R", —S(O)$_2$R', —S(O)$_2$NR'R", —SiR'R"R'", —N$_3$, substituted or unsubstituted C$_{6-10}$ aryl, substituted or unsubstituted 5- to 10-membered heteroaryl, and substituted or unsubstituted 3- to 10-membered heterocyclyl, in a number ranging from zero to (2m'+1), where m' is the total number of carbon atoms in such radical.

Substituents of interest for substituted aryl, substituted heteroaryl and substituted heterocyclyl groups include, but are not limited to, halogen, —CN, —CO$_2$R', —C(O)R', —C(O)NR'R", oxo, —OR', —OC(O)R', —OC(O)NR'R", —NO$_2$, —NR'C(O)R", —NR'C(O)NR"R'", —NR'R", —NR'CO$_2$R", —NR'S(O)$_2$R", —SR', —S(O)R', —S(O)$_2$R', —S(O)$_2$NR'R", —NR'—C(NHR").dbd.NR'", —SiR'R"R'", —N$_3$, substituted or unsubstituted C$_{1-8}$ alkyl group, substituted or unsubstituted C$_{6-10}$ aryl group, substituted or unsubstituted 5- to 10-membered heteroaryl, and substituted or unsubstituted 3- to 10-membered heterocyclyl, in a number ranging from zero to the total number of open valences on the aromatic ring system. As used above, R', R" and R'" each independently refer to a variety of groups including hydrogen, substituted or unsubstituted C$_{2-8}$ alkyl, substituted or unsubstituted C$_{2-8}$ alkenyl, substituted or unsubstituted C$_{2-8}$ alkynyl, substituted or unsubstituted aryl, substituted or unsubstituted heteroaryl, substituted or unsubstituted heterocyclyl, substituted or unsubstituted arylalkyl, and substituted or unsubstituted aryloxyalkyl. When R' and R" are attached to the same nitrogen atom, they can be combined with the nitrogen atom to form a 3-, 4-, 5-, 6-, or 7-membered ring (for example, —NR'R" includes 1-pyrrolidinyl and 4-morpholinyl).

kDa is kilo Dalton. Dalton is the standard unit that is used for indicating mass on an atomic or molecular scale.

MEK, mitogen-activated protein kinase also known as MAP2K, MEK, MAPKK, is a kinase enzyme which phosphorylates mitogen-activated protein kinase (MAPK).

MET, methyl, is a chemical group with a structure CH$_3$—.

MRAS is muscle RAS oncogene homolog. This gene encodes a member of the RAS family of small GTPases. These membrane-associated proteins function as signal transducers in multiple processes including cell growth and differentiation, and dysregulation of RAS signaling has been associated with many types of cancer. The encoded protein may play a role in the tumor necrosis factor-alpha and MAP kinase signaling pathways. Alternatively, spliced transcript variants encoding multiple isoforms have been observed for this gene.

MYH is a base excision repair gene responsible for a hereditary colon cancer syndrome. MYH is located on the short (p) arm of chromosome 1 in region 1p34.3-p32.1. MYH encodes an enzyme that removes the base adenine from mispairs (with 8-oxoguanine) that arise during the replication of oxidized DNA.

NKIRAS is NFκB inhibitor interacting RAS-like. Among its related pathways are NF-KappaB Family Pathway and TNF-alpha/NF-kB Signaling Pathway. It is also related to GTP binding and GTPase activity.

NSCLC is non-small-cell lung carcinoma. NSCLC is any type of epithelial lung cancer other than small cell lung carcinoma. As a class, NSCLCs are relatively insensitive to chemotherapy, compared to small cell carcinoma. When possible, they are primarily treated by surgical resection with curative intent, although chemotherapy is increasingly being used both pre-operatively and post-operatively.

PBS is phosphate-buffered saline. PBS is a buffer solution commonly used in biological research. It is a water-based salt solution containing sodium phosphate, sodium chloride and, in some formulations, potassium chloride and potassium phosphate.

Pharmaceutically acceptable carrier, diluent, or excipient is a carrier, diluent, or excipient compatible with the other ingredients of the formulation and not deleterious to the recipient thereof.

Pharmaceutically-acceptable salt refers to a salt which is acceptable for administration to a patient, such as a mammal (e.g., salts having acceptable mammalian safety for a given dosage regime). Such salts can be derived from pharmaceutically acceptable inorganic or organic bases and from pharmaceutically acceptable inorganic or organic acids, depending on the particular substituents found on the compounds described herein. When compounds of the present disclosure contain relatively acidic functionalities, base addition salts can be obtained by contacting the neutral form of such compounds with enough of the desired base, either neat or in a suitable inert solvent. Salts derived from pharmaceutically acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with enough of the desired acid, either neat or in a suitable inert solvent. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts. The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

PI3K is phosphatidylinositol-4,5-bisphosphate 3-kinase. PI3K(s) are a family of enzymes involved in cellular functions such as cell growth, proliferation, differentiation, motility, survival and intracellular trafficking, which in turn are involved in cancer.

RAF are a family of three serine/threonine-specific protein kinases that are related to retroviral oncogenes. RAF kinases participate in the RAS-RAF-MEK-ERK signal transduction cascade, also referred to as the mitogen-activated protein kinase (MAPK) cascade. Activation of RAF kinases requires interaction with RAS-GTPases. The three RAF kinase family members are: A-Raf, B-Raf and C-Raf (Raf-1).

Radiation therapy means exposing a subject, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including x-rays, gamma rays and neutrons.

RAL is RAS-related protein ral. Ral protein family, including RALA and RALB, belongs to the RAS family of small GTPases. Like other RAS GTPases, Ral proteins function as molecular switches alternating between inactive GDP-bound and active GT-bound states.

RAP is a GTP-binding protein also known as RAS-related proteins or simply RAP is a type of small GTPase, similar in structure to RAS. These proteins share approximately 50% amino acid identity with the classical RAS proteins and have numerous structural features in common. The most striking difference between RAP proteins and RAS proteins resides in their 61st amino acid: glutamine in RAS is replaced by threonine in RAP proteins. RAP counteracts the mitogenic function of RAS because it can interact with RAS GAPs and RAF in a competitive manner.

RAS refers to a family of related proteins which are ubiquitously expressed in all cell lineages and organs. All RAS protein family members belong to a class of protein called small GTPase that are involved in transmitting signals within cells. RAS proteins are a type of G-protein found in the cytosol that are homologous to the alpha subunit of heterotrimeric G-proteins, but unlike the alpha subunit of G proteins, a small GTPase can function independently as a hydrolase enzyme to bind to and hydrolyze a guanosine triphosphate (GTP) to form guanosine diphosphate (GDP). RAS proteins of interest include, but are not limited to hRAS, kRAS and nRAS.

REM1/REM2 is RAS (RAD and GEM)-like GTP-binding 1. The proteins are expressed in endothelial cells, where they promote reorganization of the actin cytoskeleton and morphological changes in the cells.

RERG is RAS-related and estrogen-regulated growth inhibitor. RERG, a member of the RAS superfamily of GTPases, inhibits cell proliferation and tumor formation.

SALT THEREOF refers to a compound formed when the hydrogen of an acid is replaced by a cation, such as a metal cation or an organic cation and the like. In some cases, the salt is a pharmaceutically acceptable salt, although this is not required for salts of intermediate compounds which are not intended for administration to a patient.

In addition to salt forms, the present disclosure provides compounds which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Signal transduction is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

SOS (Son of Sevenless) refers to guanine nucleotide exchange factor that act on RAS proteins and catalyzes the exchange of guanosine diphosphate (GDP) with guanosine triphosphate (GTP).

TREATING or TREATMENT as used herein refers to the treating or treatment of a disease or medical condition (such as a bacterial infection) in a patient, such as a mammal (particularly a human or a companion animal) which includes: ameliorating the disease or medical condition, i.e., eliminating or causing regression of the disease or medical condition in a patient; suppressing the disease or medical condition, i.e., slowing or arresting the development of the disease or medical condition in a patient; or alleviating the symptoms of the disease or medical condition in a patient.

Certain compounds of the present disclosure can exist in unsolvated forms as well as solvated forms, including hydrated forms. In general, both solvated forms and unsolvated forms are intended to be encompassed within the scope of the present disclosure. Certain compounds of the present disclosure may exist in multiple crystalline or amorphous forms (i.e., as polymorphs). In general, all physical forms are equivalent for the uses contemplated by the present disclosure and are intended to be within the scope of the present disclosure.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. Enantiomeric and stereoisomeric mixtures can be resolved into their component enantiomers or stereoisomers using separation techniques or chiral synthesis techniques well known to the skilled artisan. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

Certain compounds of the present disclosure possess asymmetric carbon atoms (optical centers) or double bonds; the racemates, diastereomers, geometric isomers and individual isomers (e.g., separate enantiomers) are all intended to be encompassed within the scope of the present disclosure. The compounds of the present disclosure may also contain unnatural proportions of atomic isotopes at one or more of the atoms that constitute such compounds. For example, the subject compounds may be radiolabeled with radioactive isotopes, such as for example tritium, iodine-$^{125}$I or $^{14}$C. Examples of isotopes that can be incorporated into the compounds disclosed herein include, but are not limited to, $^2$H, $^3$H, $^{11}$C, $^{13}$C, $^{14}$C, $^{15}$N, $^{18}$O, $^{17}$O, etc. All isotopic variations of the subject compounds, whether radioactive or not, are intended to be encompassed within the scope of the present disclosure.

Furthermore, except as otherwise noted, the chemical methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

As used herein and unless indicated otherwise, the term "LINKER" or "LINKAGE" refers to a linking moiety that connects two groups and has a backbone of 100 atoms or less in length. A linker or linkage may be a covalent bond that connects two groups or a chain of between 1 and 100 atoms in length, for example a chain of 1, 2, 3, 4, 5, 6, 8, 10, 12, 14, 16, 18, 20 or more carbon atoms in length, where the linker may be linear, branched, cyclic or a single atom. In some cases, the linker is a branching linker that refers to a linking moiety that connects three or more groups. In certain cases, one, two, three, four or five or more carbon atoms of a linker backbone may be optionally substituted with a sulfur, nitrogen or oxygen heteroatom. The bonds between backbone atoms may be saturated or unsaturated, and in some cases not more than one, two, or three unsaturated bonds are present in a linker backbone. The linker may include one or more substituent groups, for example with an alkyl, aryl or alkenyl group. A linker may include, without limitations, polyethylene glycol; ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone.

When describing the compounds, compositions, methods and processes of this invention, the following terms have the meanings defined herein, unless otherwise indicated.

DETAILED DESCRIPTION

As summarized above, RAS modulating compounds and methods of using the same are provided. The subject compounds comprise a core fused bicyclic group based on a quinoline-type scaffold having two fused six-membered aryl or heteroaryl rings, where one or more aromatic carbon atoms of the rings is substituted with a pyridyl-dioxane motif. The core fused bicyclic group may be linked to a cyclic group (A) through the 2-position via a linker. The linked cyclic group can be optionally substituted with an amido or a carbamate group. The compounds find use in modulating the activity of a target RAS in a sample. The target RAS can be a mutant RAS that is implicated in a disease of interest. In some cases, the subject compounds can inhibit the growth of cancer cells whose progression is driven by kRAS or a mutated kRAS. Methods of treating a subject for a RAS driven disease including administering a therapeutically effective amount of the subject compound are provided. Also provided are pharmaceutical compositions and kits which include the subject compounds.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

Modulation of RAS

The present disclosure provides RAS modulating compounds and salts thereof, and solvate, hydrate and/or prodrug form thereof, and compositions including the same. Also provided are methods that find use in the modulation of the activity of a target RAS GTPase. As used herein, the terms "RAS" and "RAS GTPase" are used interchangeably to refer to members of the class of hydrolase enzymes called, also called "small GTPase", that are involved in transmitting signals within cells. RAS subfamily members of interest which may be targeted using the subject compounds include, but are not limited to, hRAS, kRAS and nRAS. In some cases, the target RAS is one that is implicated in a cancer of interest. Exemplary target RAS proteins of interest which may be targeted using the subject compounds include, but are not limited to, DIRAS1; DIRAS2; DIRAS3; ERAS; GEM; MRAS; NKIRAS1; NKIRAS2; nRAS; RALA; RALB; RAP1A; RAP IB; RAP2A; RAP2B; RAP2C; RASD1; RASD2; RASL10A; RASL10B; RASL11A; RASL11B; RASL12; REM1; REM2; RERG; RERGL; RRAD; RRAS; RRAS2.

Modulation of RAS GTPase activity can include partial or full blockage of the Ras-Raf-MEK-ERK pathway (MAPK pathway) to result in modulation of cell proliferation. The subject compounds may modulate RAS GTPase activity by inhibiting the interaction of RAS with its upstream effectors that mediate the exchange of GDP for GTP such as SOS or its downstream effectors such as the RAF kinases. In some embodiments the subject compounds modulate synthetic lethal targets down-stream of RAS resulting in loss of RAS function and cell death. In some embodiments the synthetic lethal targets are components of mitochondrial electron transport chain, such as Complex I.

The target RAS can be a RAS GTPase or a mutant RAS GTPase which is implicated in a disease condition (e.g., as described herein). In some cases, the target RAS is a mutant RAS GTPase, such as a hRAS, a nRAS or a kRAS mutant. The mutant RAS can include a mutation at a variety of positions, such as mutation at G12, G13 or Q61. In certain cases, the RAS is a RAS-G12V mutant. The present disclosure provides RAS modulating compounds that can have anti-cancer activity. The subject compounds can interfere with the interaction of mutant RAS GTPases with their upstream and downstream targets thereby inhibiting proliferation of cancer cells.

In further describing the various aspects of the invention, the function and structure of various embodiments of RAS modulating compounds are described first in greater detail, followed by a description of methods and applications in which the compounds find use.

Compounds that Modulate RAS Activity

As summarized above, aspects of the present disclosure include RAS modulating compounds. The RAS modulating compounds are compounds which modulate the activity of a target RAS GTPase in a sample upon contact with a sample or components thereof. In some cases, by modulating the activity of a target RAS GTPase is meant that an activity related to the RAS in a cell is inhibited by 10% or more, such as 20% or more, 30% or more, 40% or more, 50% or more, 60% or more, 70% or more, 80% or more, 90% or more, or even more relative to a control, e.g., a cell not contacted with the compound of interest. Any convenient methods can be utilized in assessing modulation of the activity of RAS in a sample. In some cases, modulation of the activity of the target RAS may be assessed by observing a signal of the Ras-Raf-MEK-ERK pathway. Modulation of the signals and activities of the Ras-Raf-MEK-ERK pathway can be assessed using any convenient methods, such as those described by Kato-Stankiewicz et al. (Inhibitors of RAS/Raf-1 interaction identified by two-hybrid screening revert RAS-dependent transformation phenotypes in human cancer cells. Proc Natl Acad Sci USA. 2002; 99: 14398-403) and assays described in the Examples section herein, e.g., a phosphorylated ERK bioassay and cell morphology assay. In some instances, the types of cells in which the subject compounds exhibit activity are ones that include a mutant RAS of interest.

The sample can include a cell which includes the target RAS GTPase. In some embodiments, the RAS modulating compound decreases RAS-induced proliferation of cells that include the RAS GTPase. In some cases, the RAS-induced cellular proliferation is induced by a mutant RAS that can be targeted for inhibition using the subject compounds. By "decreases RAS-induced proliferation" is meant decreasing proliferation of the cells by 10% or more, such as 20% or more, 30% or more, 40% or more, 50% or more, 60% or more, 70% or more, 80% or more, 90% or more, or even more, relative to a control, e.g., cells not contacted with the compound of interest.

In certain embodiments, the RAS modulating compounds modulate the interaction of an activated GTP-bound RAS with a downstream protein target of the pro-growth Ras-Raf-MEK-ERK pathway. In some cases, the RAS modulating compound modulates the interaction of an activated GTP-bound RAS of interest with a RAF family protein. In certain instances, the activated GTP-bound RAS is a mutant RAS such as a hRAS, nRAS or kRAS mutant. In certain instances, the RAS modulating compound is an inhibitor of kRAS, such as a specific inhibitor of a mutated kRAS variant. The subject compound can provide a significant anti-cancer effect in patients suffering a malignancy.

Structural Features

A RAS modulating compound can include a core fused bicyclic group based on a quinoline-type scaffold having two fused six-membered aryl or heteroaryl rings, where one or more aromatic carbon atoms of the rings is substituted with a fused bicyclic pyridyl motif. In some cases, one or more aromatic carbon atoms of the rings may optionally be replaced with a nitrogen, in addition to the nitrogen atom at the N1 position of the quinoline. In some cases, the fused bicyclic group of the RAS modulating compound includes 1, 2, 3 or 4 nitrogen atoms. The core fused bicyclic group may be linked to a cyclic group (A) through the 2-position via a covalent bond or a linker. The linked cyclic group can be an aryl, substituted aryl, heteroaryl, substituted heteroaryl, heterocycle, substituted heterocycle, cycloalkyl or a substituted cycloalkyl group. In some cases, the linked cyclic group is a cycloalkyl or an aryl group substituted with an amido or a carbamate group. In some other cases, the linked cyclic group is a heterocyclic group substituted with a group selected from substituted alkyl, carboxy, substituted carboxy, and substituted alkanoyl.

A variety of substituents of interest can be included on the core fused bicyclic group or the linked cyclic group (A) of the subject compounds (e.g., a compound of any of the structural formulae described herein), such as from 1 to 5 substituents independently selected from halogen, —CN, —$NO_2$, —OH, —$OR_{1'}$, —$C(O)R_{1'}$, —$CO_2R_{1'}$, —$O(CO)R_{1'}$, —$C(O)NR_{1'}R_{2'}$, —$OC(O)NR_{1'}R_{2'}$, —$SR_{1'}$, —$SOR_{1'}$, —$SO_2R_{1'}$, —$SO_2NR_{1'}R_{2'}$, —$NR_{1'}R_{2'}$, —$NR_{1'}C(O)R_{2'}$, —$NR_{1'}C(O)_2R_{2'}$, —$NR_{1'}SO_2R_{2'}$, —$NR_{1'}(CO)NR_{2'}R_{3'}$, unsubstituted or substituted $C_{1-8}$ alkyl, unsubstituted or substituted $C_{2-8}$ alkenyl, unsubstituted or substituted $C_{2-8}$ alkynyl, unsubstituted or substituted $C_{3-8}$ cycloalkyl, unsubstituted or substituted $C_{6-10}$ aryl, unsubstituted or substituted 5- to 10-membered heteroaryl, and unsubstituted or substituted 3- to 10-membered heterocyclyl; where $R_{1'}$, $R_{2'}$ and $R_{3'}$ are each independently selected from hydrogen, unsubstituted or substituted $C_{1-6}$ haloalkyl, unsubstituted or substituted $C_{1-6}$ alkyl, unsubstituted or substituted $C_{3-8}$ cycloalkyl, unsubstituted or substituted $C_{2-6}$ alkenyl, unsubstituted or substituted $C_{2-6}$ alkynyl, unsubstituted or substituted $C_{6-10}$ aryl, unsubstituted or substituted 5- to 10-membered heteroaryl, unsubstituted or substituted 5- to 10-membered heterocycle, unsubstituted or substituted aryl-$C_{1-4}$ alkyl, unsubstituted or substituted aryl-$C_{1-4}$ alkyl, and unsubstituted or substituted aryloxy-$C_{1-4}$ alkyl; or two of $R_{1'}$, $R_{2'}$ together or $R_{1'}$ and $R_{3'}$ together with the atom(s) to which they are attached, may form an unsubstituted or substituted 5-, 6- or 7-membered ring.

Aspects of this disclosure include RAS modulating compounds of formula (I):

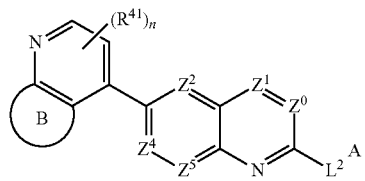

wherein:
- A is a monocyclic or bicyclic group selected from aryl, substituted aryl, heteroaryl, substituted heteroaryl, heterocycle, substituted heterocycle, cycloalkyl and substituted cycloalkyl;
- ring B is a cyclic group selected from aryl, substituted aryl, cycloalkyl, substituted cycloalkyl, heteroaryl, substituted heteroaryl, heterocycle, and substituted heterocycle;
- $Z^0$ is N or $CR^0$;
- $Z^1$ is N or $CR^1$;
- $Z^2$ is N or $CR^2$;
- $Z^3$ is N or $CR^3$;
- $Z^4$ is N or $CR^4$;
- $Z^5$ is N or $CR^5$;
- $L^2$ is covalent bond, linker having a backbone of 1-4 atoms in length (e.g., 1-3 atoms in length, such as 1, 2 or 3) or optionally substituted non-aromatic heterocycle;
- $R^0$-$R^5$ are independently selected from H, alkyl, substituted alkyl, aryl, substituted aryl, heteroaryl, substituted heteroaryl, alkoxy, substituted alkoxy, halogen, nitro, cyano, hydroxy, —$NH_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino;
- each $R^{41}$ is independently selected from H, alkyl, substituted alkyl, aryl, substituted aryl, heteroaryl, substituted heteroaryl, alkoxy, substituted alkoxy, halogen, nitro, cyano, hydroxy, —$NH_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino; and
- n is 1-2;

or a salt thereof, or a solvate, hydrate or prodrug form thereof.

In some embodiments of formula (I), A is selected from triazine, partially saturated triazine, piperidine, piperazine, 1,3-diazacyclohex-1-ene, cyclobutane, cyclohexane, bridged bicyclic piperidine, piperidin-2-one, imidazole, 1,3-diazine and partially saturated 1,3-diazine, wherein any of the A groups are optionally substituted. A partially saturated triazine is a 6 membered heterocycle including 3 nitrogen ring atoms and one (e.g., tetrahydrotriazine) or two double bonds (e.g., dihydrotriazine) in the ring. In some instances, A is triazine, such as 1,3,5-triazine. In some instances of formula (I), A is a partially saturated triazine, such as dihydro or tetrahydro 1,3,5-triazine. In some cases, A is a cyclobutane. In some cases, A is a cyclohexane. In some cases, A is a piperidine. In some cases A is a bridged cyclic piperidine. In some cases, A is a piperazine.

In some embodiments of formula (I), $L^2$ is selected from —NR'—, —$(CH_2)_n$—NR'—, —NR'—$(CH_2)_n$—, —CO—, —CONR'—, —NR'CO—, —$(CH_2)_m$—, —O—, —S—, —SO—, —$SO_2$—,

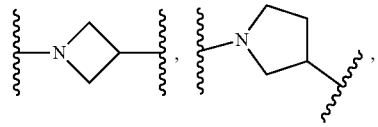

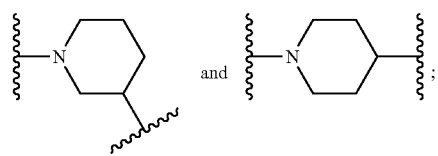

where R' is H, alkyl or substituted alkyl; m is 1-3; n is 1 or 2; and A is optionally selected from piperidine, piperazine, bridged bicyclic piperidine, butane and cyclohexane. In certain instances of $L^2$, m is 1. In some cases, m is 2. In certain cases, m is 3. In some embodiments, n is 1. In some cases, $L^2$ is —NR'—, and R' is H.

In some cases of formula (I), the compound is of formula (IIa):

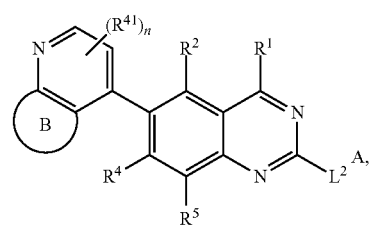

wherein A, B, $L^2$, $R^1$-$R^2$, and $R^4$-$R^5$ are as defined above.

In some cases of formula (I), the compound is of formula (IIb):

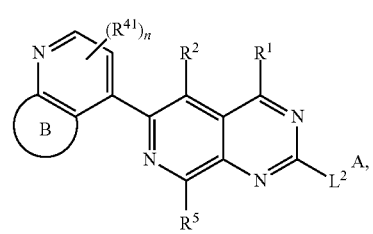

wherein A, B, $L^2$, $R^1$-$R^2$ and $R^5$ are as defined above.

In some cases of formula (I), the compound is of formula (IIc):

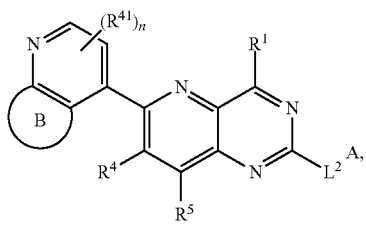

wherein A, B, $L^2$, $R^1$ and $R^4$-$R^5$ are as defined above.

In some cases of formula (I), the compound is of formula (IId):

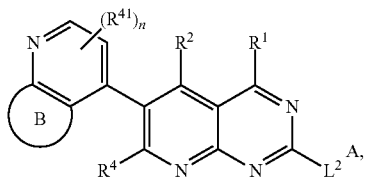

wherein A, B, $L^2$, $R^1$-$R^2$, and $R^4$ are as defined above.

In certain embodiments of any one of formulae (I)-(IId), A is a monocyclic or bicyclic aryl or cycloalkyl substituted with at least one group selected from —$NR^{1'}R^{2'}$, —$NR^{1'}C(O)R^{2'}$, —$NR^{1'}C(O)_2R^{2'}$, —$NR^{1'}SO_2R^{2'}$, —$NR^{1'}(CO)NR^{2'}R^{3'}$; where $R^{1'}$, $R^{2'}$ and $R^{3'}$ are each independently selected from hydrogen, unsubstituted or substituted $C_{1-6}$ haloalkyl, unsubstituted or substituted $C_{1-6}$ alkyl, unsubstituted or substituted $C_{3-6}$ cycloalkyl, unsubstituted or substituted $C_{2-6}$ alkenyl, unsubstituted or substituted $C_{2-6}$ alkynyl, unsubstituted or substituted $C_{6-10}$ aryl, unsubstituted or substituted 5- to 10-membered heteroaryl, unsubstituted or substituted 5- to 10-membered heterocycle, unsubstituted or substituted aryl-$C_{1-4}$ alkyl, unsubstituted or substituted aryl-$C_{1-4}$ alkyl, and unsubstituted or substituted aryloxy-$C_{1-4}$ alkyl; or two of $R^{1'}$, $R^{2'}$ together or $R^{1'}$ and $R^{3'}$ together with the atom(s) to which they are attached, may form an unsubstituted or substituted 5-, 6- or 7-membered ring.

In certain embodiments of any one of formulae (I)-(IId), A is a monocyclic or bicyclic cycloalkyl substituted with at least one group selected from —$NR^{1'}C(O)R^{2'}$, and —$NR^{1'}C(O)_2R^{2'}$, wherein $R^{1'}$ is selected from H, $C_{1-6}$ alkyl, and substituted $C_{1-6}$ alkyl, and $R^{2'}$ is selected from $C_{1-6}$ alkyl, and substituted $C_{1-6}$ alkyl. In certain cases, $R^{1'}$ is H. In certain cases, $R^{1'}$ is alkyl. In certain cases, $R^{1'}$ is substituted alkyl. In certain cases, $R^{2'}$ is selected from $C_{1-6}$ alkyl (e.g., methyl, ethyl, propyl, isopropyl, butyl, sec-butyl, t-butyl, pentyl, and hexyl).

In certain embodiments of any one of formulae (I)-(IId), A is a monocyclic or bicyclic heterocycle substituted with at least one group selected from H, alkyl, substituted alkyl, aryl, substituted aryl, carboxy, substituted carboxy, alkylsulfonyl, substituted alkylsulfonyl, alkanoyl and substituted alkanoyl.

In certain embodiments of any one of formulae (I)-(IId), A is a monocyclic or bicyclic heterocycle substituted with at least one group selected from arylalkyl, substituted arylalkyl, heteroarylalkyl, substituted heteroarylalkyl, arylalkanoyl, substituted arylalkanoyl, heteroarylalkanoyl and substituted heteroarylalkanoyl. Sometimes, A is substituted with at least one group selected from phenyl-($C_{1-6}$)alkylene, substituted phenyl-($C_{1-6}$)alkylene, phenyl-($C_{1-6}$)alkanoyl and substituted phenyl-($C_{1-6}$)alkanoyl. In some embodiments A is substituted with a group comprising a halogen-substituted phenyl group (e.g., a 4-halo-phenyl) and a ($C_{1-3}$)alkylene.

In certain embodiments of any one of formulae (I)-(IId), A is selected from one of the following structures:

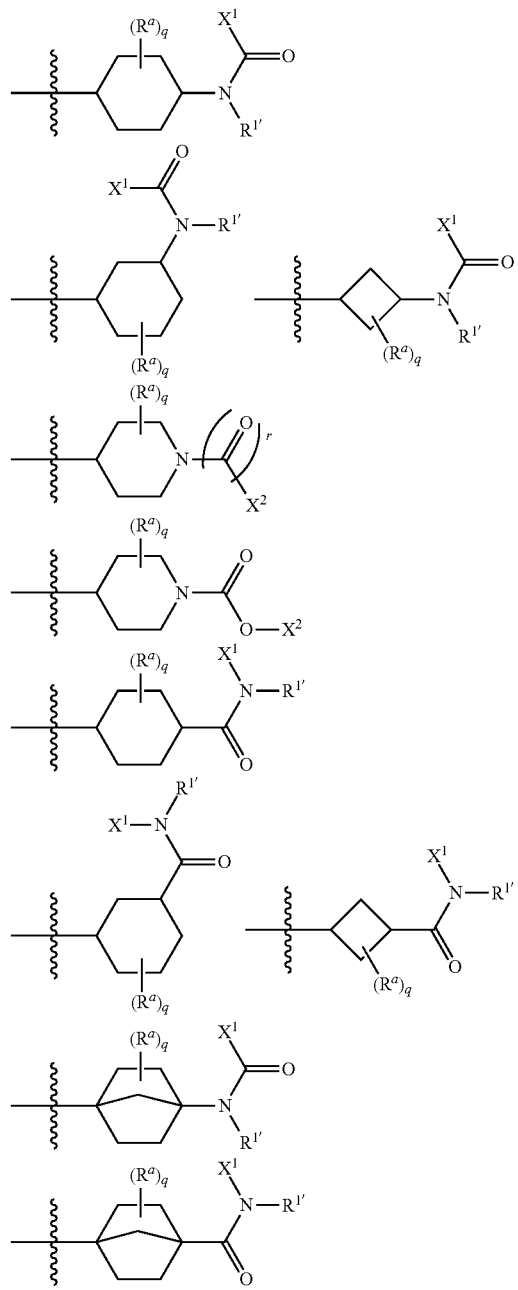

wherein:
$R^{1'}$ and $R^q$ are each independently selected from H, alkyl and substituted alkyl;
$X^1$ is selected from —$R^b$ and —$OR^b$, wherein $R^b$ is selected from alkyl, substituted alkyl, aryl, substituted aryl, heterocycle, substituted heterocycle, heteroaryl, substituted heteroaryl, cycloalkyl, and substituted cycloalkyl;

$X^2$ is selected from alkyl, substituted alkyl, aryl, substituted aryl, heterocycle, substituted heterocycle, heteroaryl, substituted heteroaryl, cycloalkyl, and substituted cycloalkyl;

q is 1-6; and r is 1 or 0.

In certain embodiments of any one of formulae (I)-(IId), A is of the following structure:

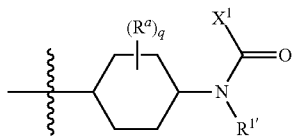

wherein:
$R^{1'}$ and $R^a$ are each independently selected from H, alkyl and substituted alkyl;

$X^1$ is selected from —$R^b$ and —$OR^b$, wherein $R^b$ is selected from alkyl, substituted alkyl, aryl, substituted aryl, heterocycle, substituted heterocycle, heteroaryl, substituted heteroaryl, cycloalkyl, and substituted cycloalkyl; and q is 1-6. In certain cases, $R^{1'}$ is H. In certain cases, each $R^a$ is H. In certain cases, $X^1$ is —$R^b$. In certain other cases, $X^1$ is —$OR^b$. In certain cases, $R^b$ is alkyl or substituted alkyl. In certain cases, $R^b$ is aryl or substituted aryl. In certain cases $R^b$ is heterocycle or substituted heterocycle. In certain cases, $R^b$ is heteroaryl or substituted heteroaryl. In certain cases, $R^b$ is cycloalkyl or substituted cycloalkyl.

In certain embodiments of any one of formulae (I)-(IId), A is of the following structure:

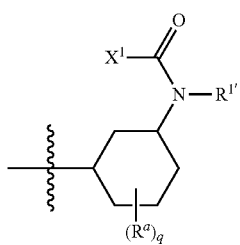

wherein:
$R^{1'}$ and $R^a$ are each independently selected from H, alkyl and substituted alkyl;

$X^1$ is selected from —$R^b$ and —$OR^b$, wherein $R^b$ is selected from alkyl, substituted alkyl, aryl, substituted aryl, heterocycle, substituted heterocycle, heteroaryl, substituted heteroaryl, cycloalkyl, and substituted cycloalkyl; and q is 1-6. In certain cases, $R^{1'}$ is H. In certain cases, each $R^a$ is H. In certain cases, $X^1$ is $R^b$. In certain other cases, $X^1$ is —$OR^b$. In certain cases, $R^b$ is alkyl or substituted alkyl. In certain cases, $R^b$ is aryl or substituted aryl. In certain cases $R^b$ is heterocycle or substituted heterocycle. In certain cases, $R^b$ is heteroaryl or substituted heteroaryl. In certain cases, $R^b$ is cycloalkyl or substituted cycloalkyl.

In certain embodiments of any one of formulae (I)-(IId), A is of the following structure:

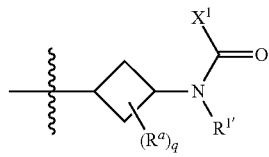

wherein:
$R^{1'}$ and $R^a$ are each independently selected from H, alkyl and substituted alkyl;

$X^1$ is selected from —$R^b$ and —$OR^b$, wherein $R^b$ is selected from alkyl, substituted alkyl, aryl, substituted aryl, heterocycle, substituted heterocycle, heteroaryl, substituted heteroaryl, cycloalkyl, and substituted cycloalkyl; and q is 1-4. In certain cases, $R^{1'}$ is H. In certain cases, each $R^a$ is H. In certain cases, $X^1$ is $R^b$. In certain other cases, $X^1$ is —$OR^b$. In certain cases, $R^b$ is alkyl or substituted alkyl. In certain cases, $R^b$ is aryl or substituted aryl. In certain cases $R^b$ is heterocycle or substituted heterocycle. In certain cases, $R^b$ is heteroaryl or substituted heteroaryl. In certain cases, $R^b$ is cycloalkyl or substituted cycloalkyl.

In certain embodiments of any one of formulae (I)-(IId), A is of the following structure:

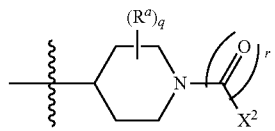

wherein:
$R^a$ are each independently selected from H, alkyl and substituted alkyl;

$X^2$ is selected from alkyl, substituted alkyl, aryl, substituted aryl, heterocycle, substituted heterocycle, heteroaryl, substituted heteroaryl, cycloalkyl, and substituted cycloalkyl;

q is 1-6; and r is 1 or 0. In certain cases, each $R^a$ is H. In certain cases, $X^2$ is alkyl or substituted alkyl. In certain cases, $X^2$ is aryl or substituted aryl. In certain cases $X^2$ is heterocycle or substituted heterocycle. In certain cases, $X^2$ is heteroaryl or substituted heteroaryl. In certain cases, $X^2$ is cycloalkyl or substituted cycloalkyl. In certain cases, r is 1. In certain other cases, r is 0, such that there is no carbonyl group between the ring nitrogen atom and $X^2$.

In certain embodiments of any one of formulae (I)-(IId), A is of the following structure:

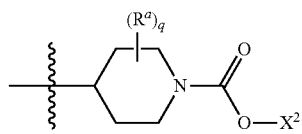

wherein:
$R^a$ are each independently selected from H, alkyl and substituted alkyl;

$X^2$ is selected from alkyl, substituted alkyl, aryl, substituted aryl, heterocycle, substituted heterocycle, heteroaryl, substituted heteroaryl, cycloalkyl, and substituted cycloalkyl; and q is 1-6. In certain cases, each $R^a$ is H. In certain cases, $X^2$ is alkyl or substituted alkyl. In certain cases, $X^2$ is aryl or substituted aryl. In certain cases $X^2$ is heterocycle or substituted heterocycle. In certain cases, $X^2$ is heteroaryl or substituted heteroaryl. In certain cases, $X^2$ is cycloalkyl or substituted cycloalkyl. In certain cases, r is 1. In certain other cases, r is 0, such that there is no carbonyl group between the ring nitrogen atom and $X^2$.

In certain embodiments of any one of formulae (I)-(IId), A is of the following structure:

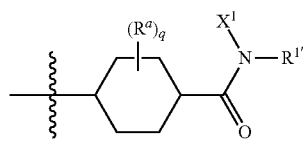

wherein:
$R^{1'}$ and $R^a$ are each independently selected from H, alkyl and substituted alkyl;
$X^1$ is selected from —$R^b$ and —$OR^b$, wherein $R^b$ is selected from alkyl, substituted alkyl, aryl, substituted aryl, heterocycle, substituted heterocycle, heteroaryl, substituted heteroaryl, cycloalkyl, and substituted cycloalkyl; and
q is 1-6. In certain cases, $R^{1'}$ is H. In certain cases, each $R^a$ is H. In certain cases, $X^1$ is $R^b$. In certain other cases, $X^1$ is —$OR^b$. In certain cases, $R^b$ is alkyl or substituted alkyl. In certain cases, $R^b$ is aryl or substituted aryl. In certain cases $R^b$ is heterocycle or substituted heterocycle. In certain cases, $R^b$ is heteroaryl or substituted heteroaryl. In certain cases, $R^b$ is cycloalkyl or substituted cycloalkyl.

In certain embodiments of any one of formulae (I)-(IId), A is of the following structure:

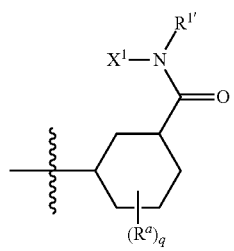

wherein:
$R^{1'}$ and $R^a$ are each independently selected from H, alkyl and substituted alkyl;
$X^1$ is selected from —$R^b$ and —$OR^b$, wherein $R^b$ is selected from alkyl, substituted alkyl, aryl, substituted aryl, heterocycle, substituted heterocycle, heteroaryl, substituted heteroaryl, cycloalkyl, and substituted cycloalkyl; and
q is 1-6. In certain cases, $R^{1'}$ is H. In certain cases, each $R^a$ is H. In certain cases, $X^1$ is $R^b$. In certain other cases, $X^1$ is —$OR^b$. In certain cases, $R^b$ is alkyl or substituted alkyl. In certain cases, $R^b$ is aryl or substituted aryl. In certain cases $R^b$ is heterocycle or substituted heterocycle. In certain cases, $R^b$ is heteroaryl or substituted heteroaryl. In certain cases, $R^b$ is cycloalkyl or substituted cycloalkyl.

In certain embodiments of any one of formulae (I)-(IId), A is of the following structure:

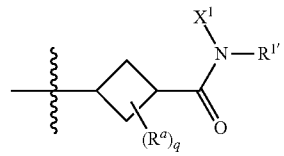

wherein:
$R^{1'}$ and $R^a$ are each independently selected from H, alkyl and substituted alkyl;
$X^1$ is selected from —$R^b$ and —$OR^b$, wherein $R^b$ is selected from alkyl, substituted alkyl, aryl, substituted aryl, heterocycle, substituted heterocycle, heteroaryl, substituted heteroaryl, cycloalkyl, and substituted cycloalkyl; and
q is 1-4. In certain cases, $R^{1'}$ is H. In certain cases, each $R^a$ is H. In certain cases, $X^1$ is $R^b$. In certain other cases, $X^1$ is —$OR^b$. In certain cases, $R^b$ is alkyl or substituted alkyl. In certain cases, $R^b$ is aryl or substituted aryl. In certain cases $R^b$ is heterocycle or substituted heterocycle. In certain cases, $R^b$ is heteroaryl or substituted heteroaryl. In certain cases, $R^b$ is cycloalkyl or substituted cycloalkyl.

In certain embodiments of any one of formulae (I)-(IId), A is of the following structure:

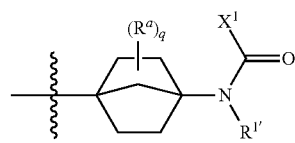

wherein:
$R^{1'}$ and $R^a$ are each independently selected from H, alkyl and substituted alkyl;
$X^1$ is selected from —$R^b$ and —$OR^b$, wherein $R^b$ is selected from alkyl, substituted alkyl, aryl, substituted aryl, heterocycle, substituted heterocycle, heteroaryl, substituted heteroaryl, cycloalkyl, and substituted cycloalkyl; and
q is 1-6. In certain cases, $R^{1'}$ is H. In certain cases, each $R^a$ is H. In certain cases, $X^1$ is —$R^b$. In certain other cases, $X^1$ is —$OR^b$. In certain cases, $R^b$ is alkyl or substituted alkyl. In certain cases, $R^b$ is aryl or substituted aryl. In certain cases $R^b$ is heterocycle or substituted heterocycle. In certain cases, $R^b$ is heteroaryl or substituted heteroaryl. In certain cases, $R^b$ is cycloalkyl or substituted cycloalkyl.

In certain embodiments of any one of formulae (I)-(IId), A is of the following structure:

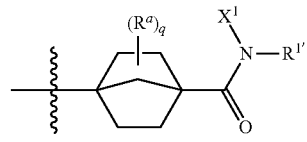

wherein:
$R^{1'}$ and $R^a$ are each independently selected from H, alkyl and substituted alkyl;
$X^1$ is selected from —$R^b$ and —$OR^b$, wherein $R^b$ is selected from alkyl, substituted alkyl, aryl, substituted aryl, heterocycle, substituted heterocycle, heteroaryl, substituted heteroaryl, cycloalkyl, and substituted cycloalkyl; and
q is 1-6. In certain cases, $R^{1'}$ is H. In certain cases, each $R^a$ is H. In certain cases, $X^1$ is $R^b$. In certain other cases, $X^1$ is —OR$^b$. In certain cases, R$^b$ is alkyl or substituted alkyl. In certain cases, R$^b$ is aryl or substituted aryl. In certain cases R$^b$ is heterocycle or substituted heterocycle. In certain cases, R$^b$ is heteroaryl or substituted heteroaryl. In certain cases, R$^b$ is cycloalkyl or substituted cycloalkyl.

In certain embodiments of any one of formulae (I)-(IId), A is selected from the following compounds:

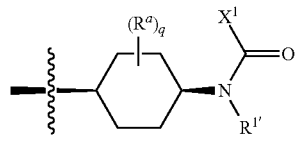

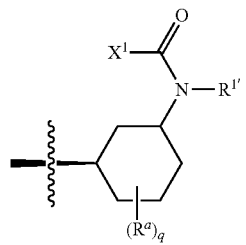

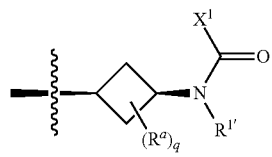

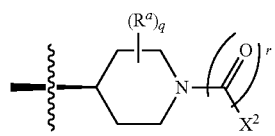

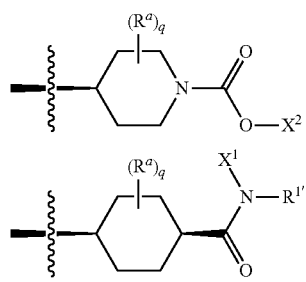

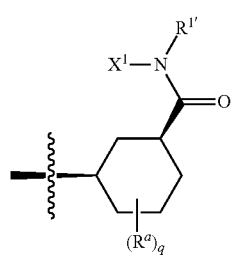

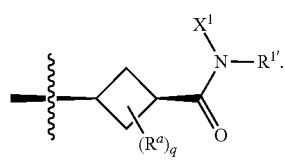

In certain embodiments of any one of formulae (I)-(IId), ring B is selected from one of the following structures:

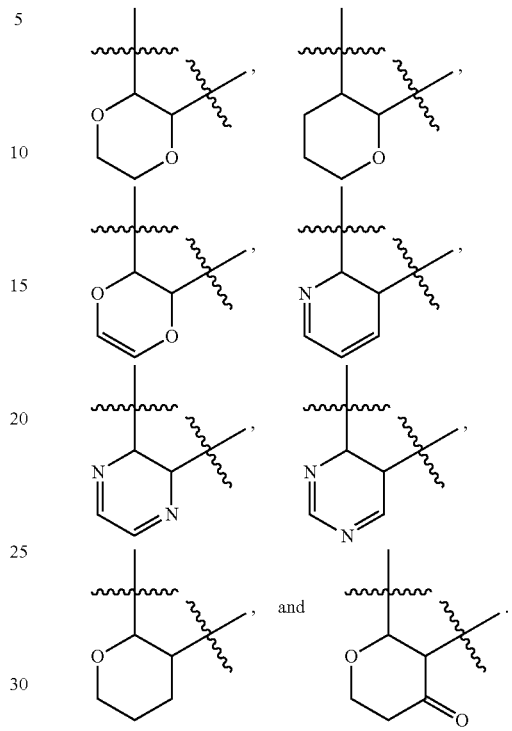

In some embodiments of formula (I), the compound is of formula (IIIa):

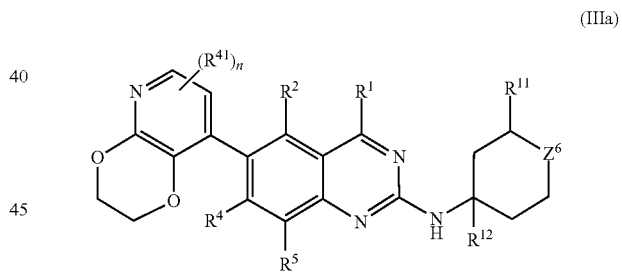

(IIIa)

wherein:

$Z^6$ is NR$^6$ or C(R$^6$)$_2$;

each R$^6$ is independently selected from H, alkyl, substituted alkyl, aryl, substituted aryl, heterocycle, substituted heterocycle, heteroaryl, substituted heteroaryl, alkoxy, substituted alkoxy, halogen, nitro, cyano, hydroxy, —NH$_2$, substituted amino, amido, substituted amido, carbamate, substituted carbamate, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino; and R$^{11}$ is selected from H, alkyl, and substituted alkyl;

R$^{12}$ is selected from H, alkyl, and substituted alkyl; or

R$^{12}$ and one Re group together with the atoms to which they are attached form a bicyclic group.

In certain embodiments of formula (IIIa), Z$^6$ is C(R$^6$)$_2$; wherein one R$^6$ group is H and the other R$^6$ group is selected from —NR¹R²', —NR¹'C(O)R²', —NR¹'C(O)₂R²', —NR¹'SO₂R²', —NR¹'(CO)NR²'R³'; where R¹', R²' and R³' are each independently selected from hydrogen, unsubstituted or substituted $C_{1-6}$ haloalkyl, unsubstituted or substituted $C_{1-6}$ alkyl, unsubstituted or substituted $C_{3-6}$ cycloalkyl, unsubstituted or substituted $C_{2-6}$ alkenyl, unsubstituted or substituted $C_{2-6}$ alkynyl, unsubstituted or substituted $C_{6-10}$ aryl, unsubstituted or substituted 5- to 10-membered heteroaryl, unsubstituted or substituted 5- to 10-membered heterocycle, unsubstituted or substituted aryl-$C_{1-4}$alkyl, unsubstituted or substituted aryl-$C_{1-4}$alkyl, and unsubstituted or substituted aryloxy-$C_{1-4}$ alkyl.

In certain embodiments of formula (IIIa), $Z^6$ is $C(R^6)_2$, where one $R^6$ group is H, and the other $R^6$ group is selected from —NR¹'C(O)R²', or —NR¹'C(O)₂R²'; wherein R¹' is selected from H, $C_{1-6}$ alkyl, and substituted $C_{1-6}$ alkyl, and R²' is selected from $C_{1-6}$ alkyl, and substituted $C_{1-6}$ alkyl. In certain cases, R¹' is H. In certain cases, R¹' is alkyl. In certain cases, R¹' is substituted alkyl. In certain cases, R²' is selected from $C_{1-6}$ alkyl (e.g., methyl, ethyl, propyl, isopropyl, butyl, sec-butyl, t-butyl, pentyl, and hexyl).

In certain embodiments of formula (IIIa), $Z^6$ is $C(R^6)_2$, where one $R^6$ group forms a carbon-carbon bond with $R^{12}$ to form a bicyclic ring system. In certain cases, the other $R^6$ group is selected from —NR¹'R²', —NR¹'C(O)R²', —NR¹'C(O)₂R²', —NR¹'SO₂R²', —NR¹'(CO)NR²'R³'; where R¹', R²' and R³' are each independently selected from hydrogen, unsubstituted or substituted $C_{1-6}$ haloalkyl, unsubstituted or substituted $C_{1-6}$ alkyl, unsubstituted or substituted $C_{3-6}$ cycloalkyl, unsubstituted or substituted $C_{2-6}$ alkenyl, unsubstituted or substituted $C_{2-6}$ alkynyl, unsubstituted or substituted $C_{6-10}$ aryl, unsubstituted or substituted 5- to 10-membered heteroaryl, unsubstituted or substituted 5- to 10-membered heterocycle, unsubstituted or substituted aryl-$C_{1-4}$ alkyl, unsubstituted or substituted aryl-$C_{1-4}$ alkyl, and unsubstituted or substituted aryloxy-$C_{1-4}$ alkyl. In certain other cases, the other $R^6$ group is selected from —NR¹'C(O)R²', or —NR¹'C(O)₂R²'; wherein R¹' is selected from H, $C_{1-4}$ alkyl, and substituted $C_{1-6}$ alkyl, and R²' is selected from $C_{1-6}$ alkyl, and substituted $C_{1-6}$ alkyl. In certain cases, R¹' is H. In certain cases, R¹' is alkyl. In certain cases, R¹' is substituted alkyl. In certain cases, R²' is selected from $C_{1-6}$ alkyl (e.g., methyl, ethyl, propyl, isopropyl, butyl, sec-butyl, t-butyl, pentyl, and hexyl).

In certain other embodiments of formula (IIIa), $Z^6$ is $NR^6$; and $R^6$ is selected from —C(O)R²', —C(O)₂R²', —SO₂R²', —(CO)NR²'R³', —(CH₂)$_m$R²'; where R¹', R²' and R³' are each independently selected from hydrogen, unsubstituted or substituted $C_{1-6}$ haloalkyl, unsubstituted or substituted $C_{1-6}$ alkyl, unsubstituted or substituted $C_{3-6}$ cycloalkyl, unsubstituted or substituted $C_{2-6}$ alkenyl, unsubstituted or substituted $C_{2-6}$ alkynyl, unsubstituted or substituted $C_{6-10}$ aryl, unsubstituted or substituted 5- to 10-membered heteroaryl, unsubstituted or substituted 5- to 10-membered heterocycle, unsubstituted or substituted aryl-$C_{1-4}$ alkyl, unsubstituted or substituted aryl-$C_{1-4}$ alkyl, and unsubstituted or substituted aryloxy-$C_{1-4}$ alkyl; and m is 1 and 5.

In some embodiments of formula (IIIa), $Z^6$ is $NR^6$; and $R^6$ is selected from —C(O)R²', —C(O)₂R²', and —(CH₂)$_m$R²', wherein m is 1, and R²' is selected from $C_{1-6}$ alkyl, substituted $C_{1-6}$ alkyl, $C_{3-6}$ cycloalkyl, substituted $C_{3-6}$ cycloalkyl, $C_{6-10}$ aryl, substituted $C_{6-10}$ aryl, 5- to 10-membered heteroaryl, and substituted 5- to 10-membered heteroaryl.

In certain embodiments of formula (IIIa), the compound is of formula (IVa) or (IVb):

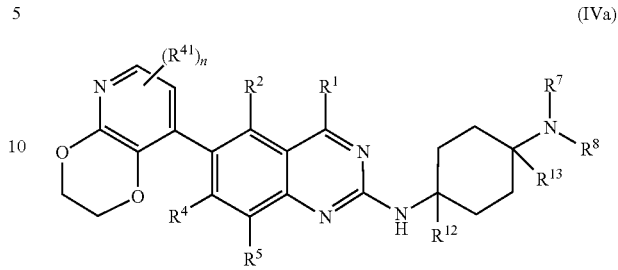

(IVa)

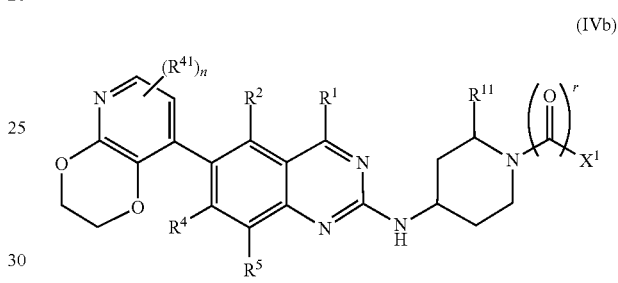

(IVb)

wherein:

$X^1$ is selected from —$R^b$ and —$OR^b$, wherein $R^b$ is selected from alkyl, substituted alkyl, aryl, substituted aryl, heterocycle, substituted heterocycle, heteroaryl, substituted heteroaryl, cycloalkyl, and substituted cycloalkyl;

$R^7$ is selected from H, alkyl, and substituted alkyl;

$R^8$ is selected from carboxy, substituted carboxy, sulfonyl, substituted sulfonyl, alkanoyl and substituted alkanoyl;

$R^{11}$ is selected from H, alkyl, and substituted alkyl;

$R^{12}$ and $R^{13}$ are each independently selected from H, alkyl, and substituted alkyl; or $R^{12}$ and $R^{13}$ together with the atoms to which they are attached form a bicyclic group; and r is 1 or 0.

In certain instances, the compound of formula (IIIa) is of formula (IVa), wherein $R^7$ is H, and $R^8$ is selected from —C(O)R²', —C(O)₂R²', and —SO₂R²'; where R²' is selected from hydrogen, unsubstituted or substituted $C_{1-6}$ haloalkyl, unsubstituted or substituted $C_{1-6}$ alkyl, unsubstituted or substituted $C_{3-6}$ cycloalkyl, unsubstituted or substituted $C_{2-6}$ alkenyl, unsubstituted or substituted $C_{2-6}$ alkynyl, unsubstituted or substituted $C_{6-10}$ aryl, unsubstituted or substituted 5- to 10-membered heteroaryl, unsubstituted or substituted 5- to 10-membered heterocycle, unsubstituted or substituted aryl-$C_{1-4}$ alkyl, unsubstituted or substituted aryl-$C_{1-4}$ alkyl, and unsubstituted or substituted aryloxy-$C_{1-4}$ alkyl. In certain instances $R^8$ is —C(O)R²'. In certain cases, $R^8$ is —C(O)₂R²'.

In certain instances, the compound of formula (IIIa) is of formula (IVa), where $R^{12}$ and $R^{13}$ together form a carbon-carbon bond to form a bicyclic system.

In certain embodiments, the compound of formula (IVa) is of the formula (IVc):

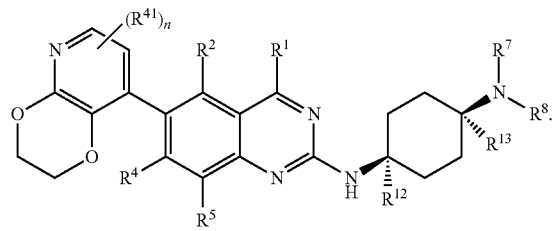
(IVc)

In certain other cases, the compound of formula (IIIa) is of formula (IVb) wherein, $X^1$ is selected from —$R^b$ and —$OR^b$, wherein $R^b$ is selected from alkyl, substituted alkyl, aryl, substituted aryl, heterocycle, substituted heterocycle, heteroaryl, substituted heteroaryl, cycloalkyl, and substituted cycloalkyl; $R^{11}$ is H, or $C_{1-3}$ alkyl; and r is 1 or 0. In certain cases, r is 1, and $X^1$ is $OR^b$. In certain cases, r is 0, and $X^1$ is $R^b$. In certain cases, $R^b$ is alkyl or substituted alkyl. In certain cases, $R^b$ is aryl or substituted aryl. In certain cases $R^b$ is heterocycle or substituted heterocycle. In certain cases, $R^b$ is heteroaryl or substituted heteroaryl. In certain cases, $R^b$ is cycloalkyl or substituted cycloalkyl.

In certain embodiments, the compound of formula (IVb) is of the formula (IVd):

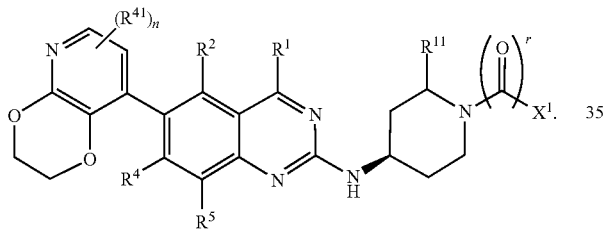
(IVd)

In certain instances of any of formula (IIIa)-(IVd), $R^1$ is selected from H, alkyl, or substituted alkyl. In some cases, $R^2$ is $C_{1-6}$ alkyl. In some cases, $R^2$ is methyl. In certain cases, $R^2$ is halogen. In certain cases, $R^2$ is fluoride.

In certain instances of any of formula (IIIa)-(IVd), $R^2$ is selected from H, alkyl, or substituted alkyl. In some cases, $R^2$ is $C_{1-6}$ alkyl. In some cases, $R^2$ is H. In certain cases, $R^2$ is halogen. In certain cases, $R^2$ is fluoride.

In certain instances of any of formula (IIIa)-(IVd), $R^4$ is selected from H, alkyl, or substituted alkyl. In some cases, $R^2$ is $C_{1-6}$ alkyl. In some cases, $R^4$ is H. In certain cases, $R^4$ is halogen. In certain cases, $R^4$ is fluoride.

In certain instances of any of formula (IIIa)-(IVd), $R^5$ is selected from H, alkyl, or substituted alkyl. In some cases, $R^2$ is $C_{1-6}$ alkyl. In some cases, $R^5$ is H. In certain cases, $R^5$ is halogen. In certain cases, $R^5$ is fluoride.

In certain embodiments of any of the formulae (IIIa)-(IVd), the pyridyl-dioxane motif may be replaced with a pyridyl-N-oxide dioxane motif of the following structure:

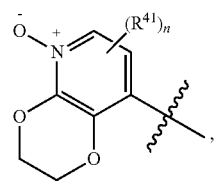

wherein $R^{41}$ and n are as described herein above.

In certain embodiments, the subject compound is of one of the following structures in Table 1:

TABLE 1A

| Compound No. | Structure |
|---|---|
| 1A | 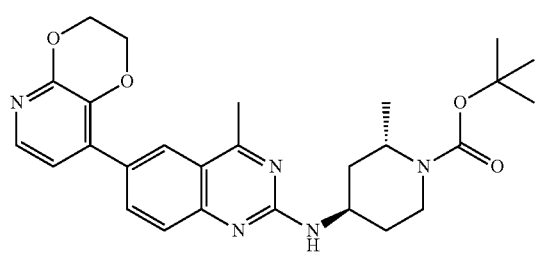 [SMILES: Cc1nc(N[C@@H]2CCN(C(=O)OC(C)(C)C)[C@@H](C)C2)nc2ccc(-c3ccnc4c3OCCO4)cc12] |

TABLE 1A-continued
| Compound No. | Structure |
|---|---|
| 2A | 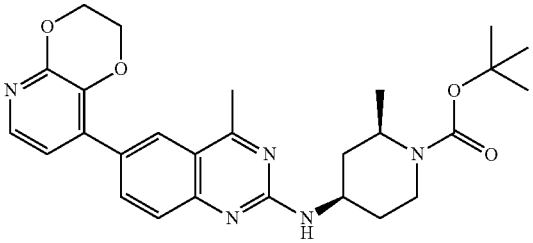 [SMILES: Cc1nc(N[C@@H]2CCN(C(=O)OC(C)(C)C)[C@H](C)C2)nc2ccc(-c3ccnc4c3OCCO4)cc12] |
| 3A | 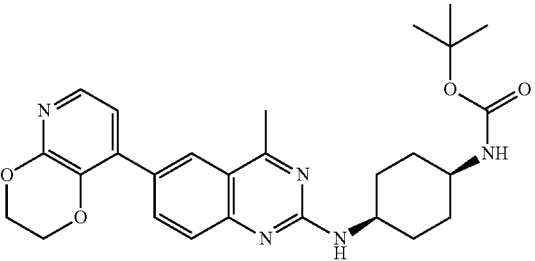 [SMILES: Cc1nc(N[C@H]2CC[C@@H](NC(=O)OC(C)(C)C)CC2)nc2ccc(-c3ccnc4c3OCCO4)cc12] |
| 4A | 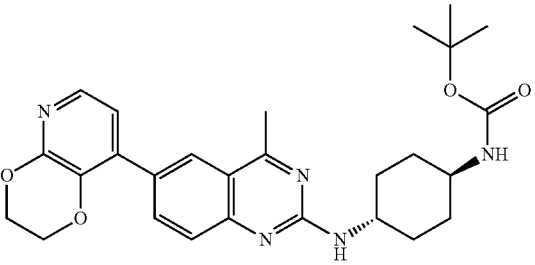 [SMILES: Cc1nc(N[C@H]2CC[C@H](NC(=O)OC(C)(C)C)CC2)nc2ccc(-c3ccnc4c3OCCO4)cc12] |
| 5A | 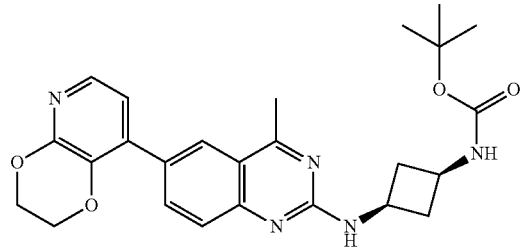 [SMILES: Cc1nc(N[C@H]2C[C@@H](NC(=O)OC(C)(C)C)C2)nc2ccc(-c3ccnc4c3OCCO4)cc12] |
| 6A | 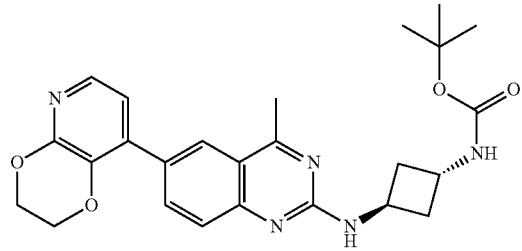 [SMILES: Cc1nc(N[C@H]2C[C@H](NC(=O)OC(C)(C)C)C2)nc2ccc(-c3ccnc4c3OCCO4)cc12] |
| 7A | 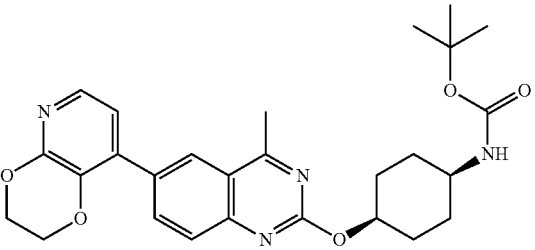 [SMILES: Cc1nc(O[C@H]2CC[C@@H](NC(=O)OC(C)(C)C)CC2)nc2ccc(-c3ccnc4c3OCCO4)cc12] |

TABLE 1A-continued
| Compound No. | Structure |
|---|---|
| 8A | 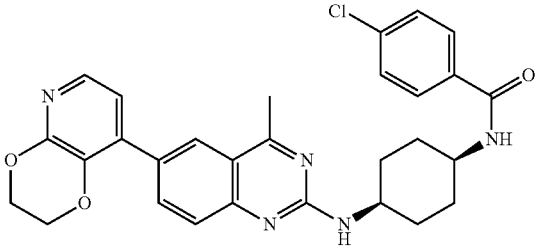 [SMILES: Cc1nc(N[C@H]2CC[C@@H](NC(=O)c3ccc(Cl)cc3)CC2)nc2ccc(-c3ccnc4c3OCCO4)cc12] |
| 9A | 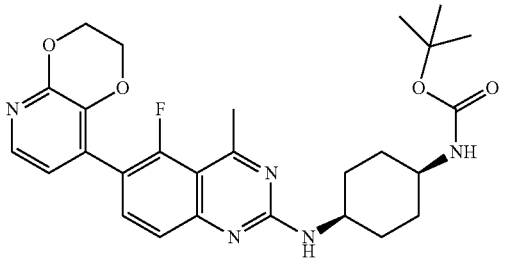 [SMILES: Cc1nc(N[C@H]2CC[C@@H](NC(=O)OC(C)(C)C)CC2)nc2ccc(-c3ccnc4c3OCCO4)c(F)c12] |
| 10A | 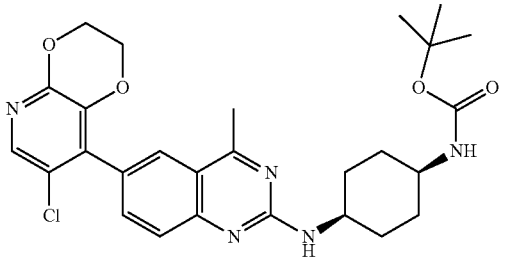 [SMILES: Cc1nc(N[C@H]2CC[C@@H](NC(=O)OC(C)(C)C)CC2)nc2ccc(-c3c(Cl)cnc4c3OCCO4)cc12] |
| 11A | 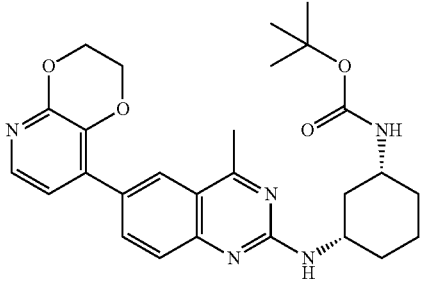 [SMILES: Cc1nc(N[C@H]2CCC[C@@H](NC(=O)OC(C)(C)C)C2)nc2ccc(-c3ccnc4c3OCCO4)cc12] |
| 12A | 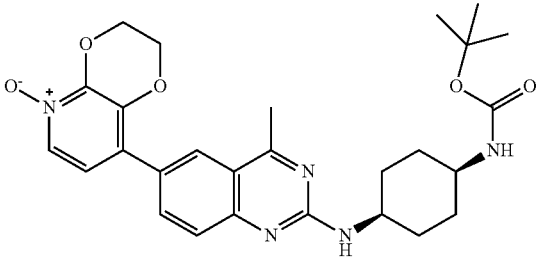 [SMILES: Cc1nc(N[C@H]2CC[C@@H](NC(=O)OC(C)(C)C)CC2)nc2ccc(-c3cc[n+]([O-])c4c3OCCO4)cc12] |

TABLE 1A-continued

| Compound No. | Structure |
|---|---|
| 13A | 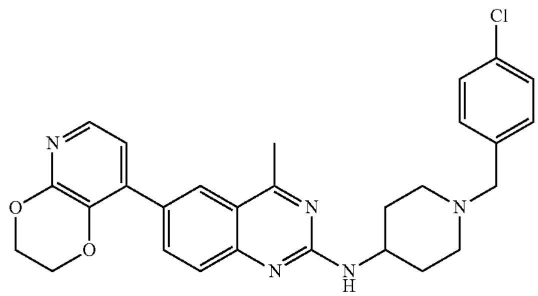 [SMILES: Cc1nc(NC2CCN(Cc3ccc(Cl)cc3)CC2)nc2ccc(-c3ccnc4c3OCCO4)cc12] |
| 14A | 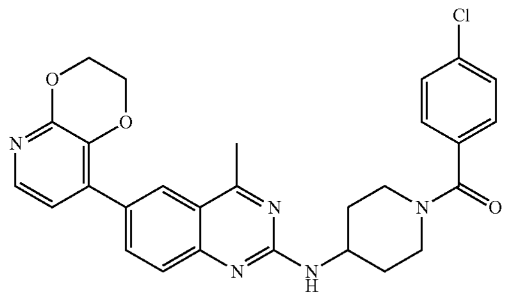 [SMILES: Cc1nc(NC2CCN(C(=O)c3ccc(Cl)cc3)CC2)nc2ccc(-c3ccnc4c3OCCO4)cc12] |
| 15A | 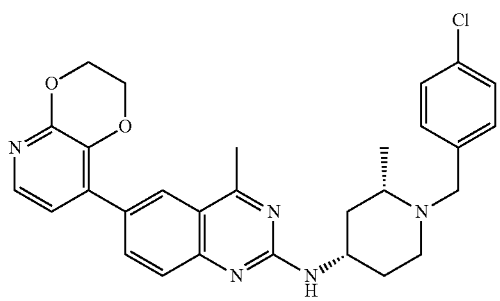 [SMILES: Cc1nc(N[C@H]2CCN(Cc3ccc(Cl)cc3)[C@@H](C)C2)nc2ccc(-c3ccnc4c3OCCO4)cc12] |
| 16A | 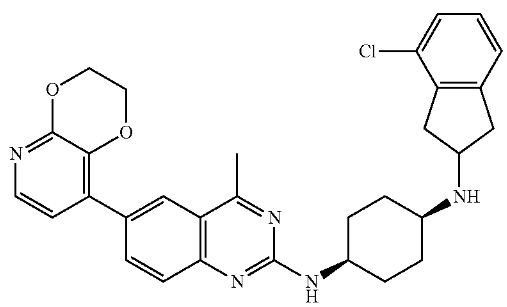 [SMILES: Cc1nc(N[C@H]2CC[C@@H](NC3Cc4cccc(Cl)c4C3)CC2)nc2ccc(-c3ccnc4c3OCCO4)cc12] |
| 17A | 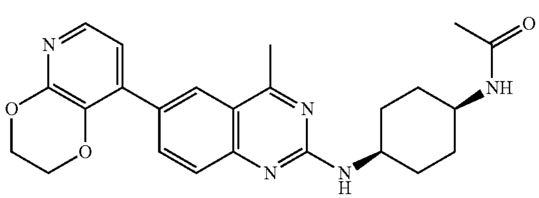 [SMILES: CC(=O)N[C@H]1CC[C@@H](Nc2nc(C)c3cc(-c4ccnc5c4OCCO5)ccc3n2)CC1] |
| 18A | 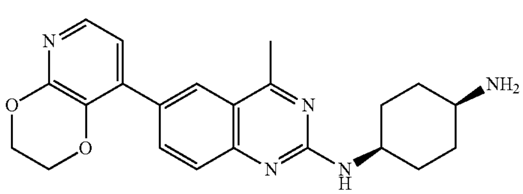 [SMILES: Cc1nc(N[C@H]2CC[C@@H](N)CC2)nc2ccc(-c3ccnc4c3OCCO4)cc12] |

TABLE 1A-continued

| Compound No. | Structure |
|---|---|
| 19A | 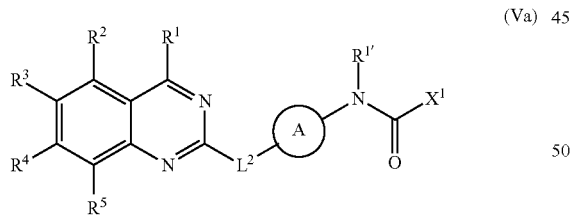 |
| 20A | 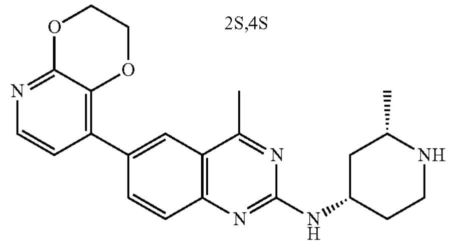 [SMILES: Cc1nc(N[C@H]2CCN[C@@H](C)C2)nc2ccc(-c3ccnc4c3OCCO4)cc12] |
| 21A | 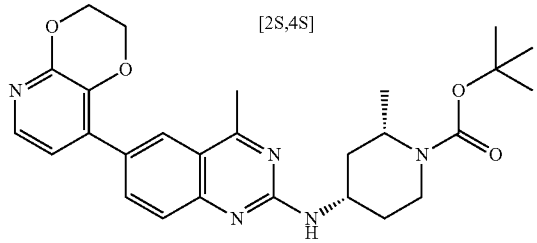 [SMILES: Cc1nc(N[C@H]2CCN(C(=O)OC(C)(C)C)[C@@H](C)C2)nc2ccc(-c3ccnc4c3OCCO4)cc12] |

In certain embodiments, the subject compound is of the formula (Va):

(Va)

wherein:
ring A is a monocyclic or bicyclic group selected from aryl, substituted aryl, heteroaryl, substituted heteroaryl, heterocycle, substituted heterocycle, cycloalkyl and substituted cycloalkyl;
$L^2$ is a linker having a backbone of 1-4 atoms in length (e.g., 1-3 atoms in length, such as 1, 2 or 3);
$R^{1'}$ is selected from H, alkyl and substituted alkyl;
$X^1$ is selected from $-R^b$ and $-OR^b$, wherein $R^b$ is selected from alkyl, substituted alkyl, aryl, substituted aryl, heterocycle, substituted heterocycle, heteroaryl, substituted heteroaryl, cycloalkyl, and substituted cycloalkyl;

$R^1$-$R^2$, and $R^4$-$R^5$ are independently selected from H, alkyl, substituted alkyl, aryl, substituted aryl, heteroaryl, substituted heteroaryl, alkoxy, substituted alkoxy, halogen, nitro, cyano, hydroxy, $-NH_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino;

$R^3$ is selected from one of the following structures:

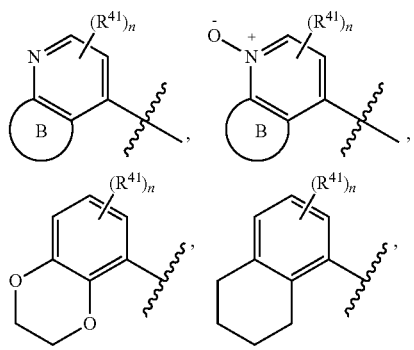

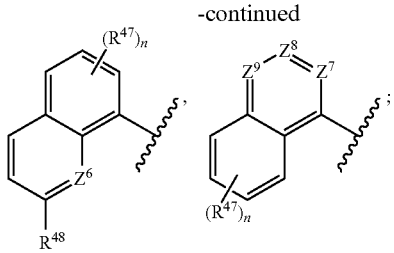

each R⁴¹ is independently selected from H, alkyl, substituted alkyl, aryl, substituted aryl, heteroaryl, substituted heteroaryl, alkoxy, substituted alkoxy, halogen, nitro, cyano, hydroxy, —NH₂, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino;

ring B is a cyclic group selected from aryl, substituted aryl, cycloalkyl, substituted cycloalkyl, heteroaryl, substituted heteroaryl, heterocycle, and substituted heterocycle;

Z⁷-Z⁹ are each independently N or CR⁴⁹;

each R⁴⁷ is independently selected from H and halogen; and

R⁴⁸-R⁴⁹ are each independently selected from H, alkyl and substituted alkyl; and n is 1-3.

In certain embodiments of formula (Va), R³ is a six membered cyclic group selected from heteroaryl, substituted heteroaryl, heterocycle, and substituted heterocycle. In certain embodiments of formula (Va), R³ is selected from one of the following structures:

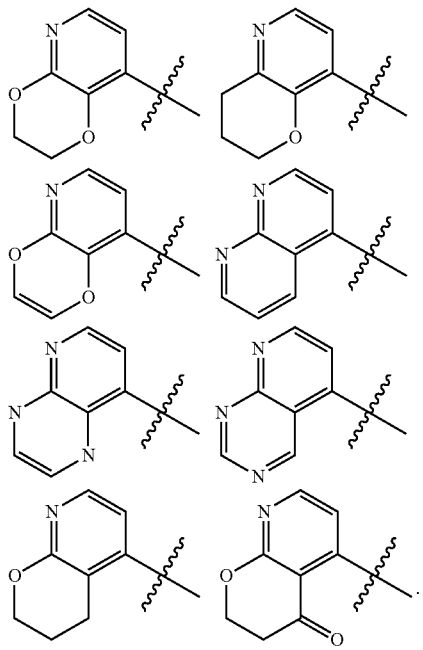

In certain embodiments of formula (Va), A is selected from a monocyclic or bicyclic aryl, substituted aryl, cycloalkyl, and substituted cycloalkyl. In certain cases, A is a cyclobutyl, or substituted cyclobutyl. In certain cases, A is cyclohexyl, or substituted cyclohexyl.

In some embodiments of formula (Va), L² is selected from —NR'—, —(CH₂)ₙ—NR'—, —NR'—(CH₂)ₙ—, —CO—, —CONR'—, —NR'CO—, —(CH₂)ₘ—,

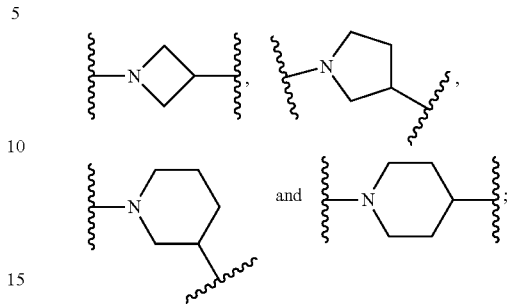

where R' is H, alkyl or substituted alkyl; m is 1-3; n is 1 or 2; and A is optionally selected from piperidine, piperazine, bridged bicyclic piperidine, butane and cyclohexane. In certain instances of L², m is 1. In some cases, m is 2. In certain cases, m is 3. In some embodiments, n is 1. In some cases, L² is —NR'—, and R' is H.

In certain embodiments, the subject compound is of the formula (Vb):

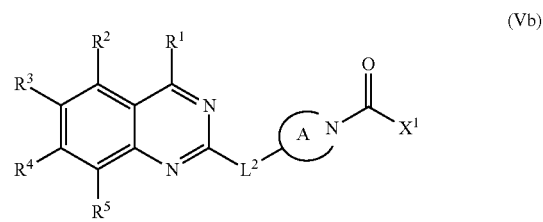

(Vb)

wherein:
ring A is a monocyclic or bicyclic group selected from heteroaryl, substituted heteroaryl, heterocycle, and substituted heterocycle;

L² is a linker having a backbone of 1-4 atoms in length (e.g., 1-3 atoms in length, such as 1, 2 or 3);

X¹ is selected from —Rᵇ and —ORᵇ, wherein Rᵇ is selected from alkyl, substituted alkyl, aryl, substituted aryl, heterocycle, substituted heterocycle, heteroaryl, substituted heteroaryl, cycloalkyl, and substituted cycloalkyl;

R¹-R², and R⁴-R⁵ are independently selected from H, alkyl, substituted alkyl, aryl, substituted aryl, heteroaryl, substituted heteroaryl, alkoxy, substituted alkoxy, halogen, nitro, cyano, hydroxy, —NH₂, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino;

R³ is selected from one of the following structures:

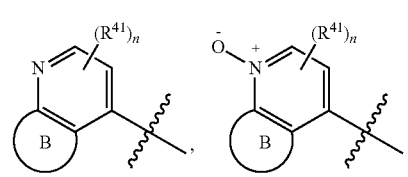

-continued

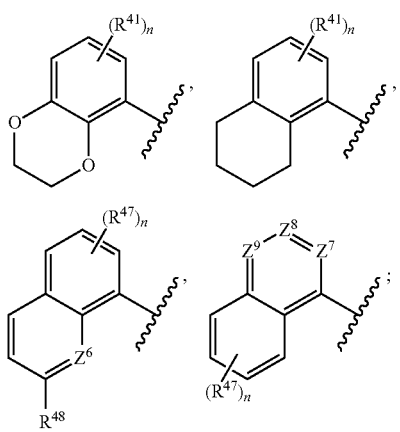

each R[41] is independently selected from H, alkyl, substituted alkyl, aryl, substituted aryl, heteroaryl, substituted heteroaryl, alkoxy, substituted alkoxy, halogen, nitro, cyano, hydroxy, —NH$_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino;

ring B is a cyclic group selected from aryl, substituted aryl, cycloalkyl, substituted cycloalkyl, heteroaryl, substituted heteroaryl, heterocycle, and substituted heterocycle;

$Z^7$-$Z^9$ are each independently N or CR$^{49}$;

each R$^{47}$ is independently selected from H and halogen; and

R$^{48}$-R$^{49}$ are each independently selected from H, alkyl and substituted alkyl; and n is 1-3.

In certain embodiments of formula (Vb), R$^3$ is a six membered cyclic group selected from heteroaryl, substituted heteroaryl, heterocycle, and substituted heterocycle. In certain embodiments of formula (Vb), R$^3$ is selected from one of the following structures:

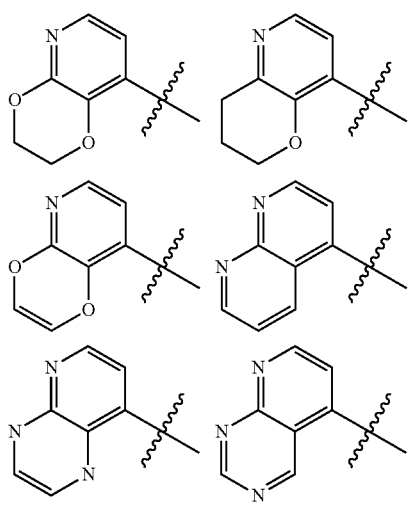

-continued

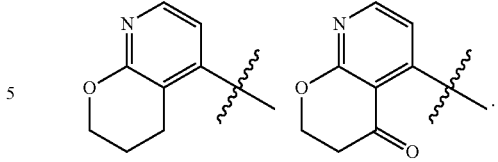

In certain embodiments of formula (Vb), A is selected from a monocyclic heterocycle or heteroaryl group. In some cases, A is selected from a bicyclic heterocycle or heteroaryl group. In some cases, A is a bridged bicyclic heterocycle. In certain cases, A is a piperidine. In certain cases, A is bridged bicyclic piperidine.

In some embodiments of formula (Va), L$^2$ is selected from —NR'—, —(CH$_2$)$_n$—NR'—, —NR'—(CH$_2$)$_n$—, —CO—, —CONR'—, —NR'CO—, —(CH$_2$)$_m$—,

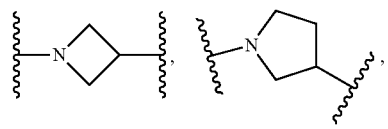

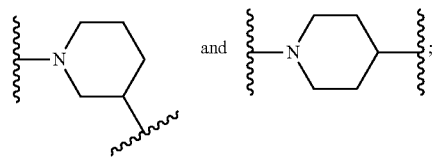

where R' is H, alkyl or substituted alkyl; m is 1-3; n is 1 or 2; and A is optionally selected from piperidine, piperazine, bridged bicyclic piperidine, butane and cyclohexane. In certain instances of L$^2$, m is 1. In some cases, m is 2. In certain cases, m is 3. In some embodiments, n is 1. In some cases, L$^2$ is —NR'—, and R' is H.

In certain instances of the compound of formula (Va) or (Vb), R$^1$ is selected from H, alkyl, or substituted alkyl. In some cases, R$^1$ is C$_{1-6}$ alkyl. In some cases, R$^1$ is methyl. In some cases, R$^1$ is halogen. In some cases, R$^1$ is Fluoride.

In certain instances of the compound of formula (Va) or (Vb), R$^2$ is selected from H, alkyl, or substituted alkyl. In some cases, R$^2$ is C$_{1-6}$ alkyl. In some cases, R$^2$ is H. In some cases, R$^2$ is halogen. In some cases, R$^2$ is Fluoride.

In certain instances of the compound of formula (Va) or (Vb), R$^4$ is selected from H, alkyl, or substituted alkyl. In some cases, R$^2$ is C$_{1-6}$ alkyl. In some cases, R$^4$ is H. In some cases, R$^4$ is halogen. In some cases, R$^4$ is Fluoride.

In certain instances of the compound of formula (Va) or (Vb), R$^5$ is selected from H, alkyl, or substituted alkyl. In some cases, R$^2$ is C$_{1-6}$ alkyl. In some cases, R$^5$ is H. In some cases, R$^4$ is halogen. In some cases, R$^4$ is Fluoride.

In some cases, R$^3$ is replaced with a halogen atom. In some cases, R$^3$ is selected from chloride, bromide or fluoride.

In certain instances of the compound of formula (Va) or (Vb) described herein, R$^3$ is of one of the following structures:

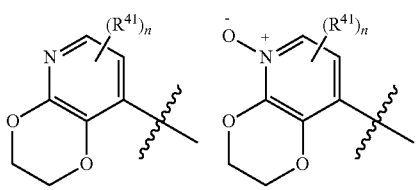

wherein:
n is 1-2; and
each $R^{41}$ is independently selected from H, alkyl, substituted alkyl, aryl, substituted aryl, heteroaryl, substituted heteroaryl, alkoxy, substituted alkoxy, halogen, nitro, cyano, hydroxy, —$NH_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino. In certain cases, each $R^{41}$ is H.

In certain instances of the compound of formula (Va) or (Vb) described herein, $R^3$ is of the following structure:

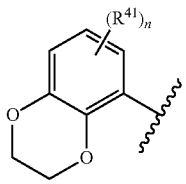

wherein:
n is 1-3; and
each $R^{41}$ is independently selected from H, alkyl, substituted alkyl, aryl, substituted aryl, heteroaryl, substituted heteroaryl, alkoxy, substituted alkoxy, halogen, nitro, cyano, hydroxy, —$NH_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino. In certain cases, each $R^{41}$ is H.

In certain instances of the compound of formula (Va) or (Vb) described herein, $R^3$ is of the following structure:

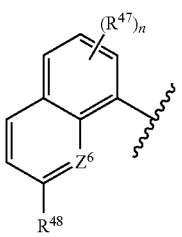

wherein:
$Z^6$ is N or $CR^{49}$;
n is 1-3; and
each $R^{47}$ is independently selected from H and halogen; and
$R^{48}$-$R^{49}$ are each independently selected from H, alkyl and substituted alkyl. In certain cases, $Z^6$ is N. In certain cases, each $R^{41}$ is H. In certain cases, $R^{48}$ is H. In certain other cases, $R^{48}$ is alkyl. In certain cases, $R^{48}$ is —$CH_3$. In certain cases, one $R^{47}$ group is halogen. In certain cases, one $R^{47}$ group is F. In certain cases $R^3$ group has the following structure:

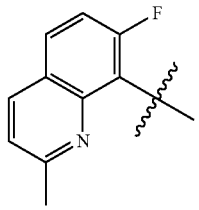 [SMILES: *c1c(F)ccc2ccc(C)nc12]

In certain instances of the compound of formula (Va) or (Vb) described herein, $R^3$ is of the following structure:

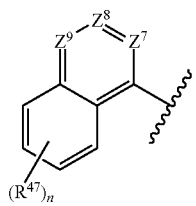

wherein:
$Z^7$-$Z^9$ are each independently N or $CR^{49}$;
n is 1-3; and
each $R^{47}$ is independently selected from H and halogen; and
each $R^{49}$ is independently selected from H, alkyl and substituted alkyl. In certain cases, $Z^9$ is N. In certain cases Z is N; and $Z^7$-$Z^8$ are each $CR^{49}$, where $R^{49}$ is H. In certain cases, each $R^{47}$ is H. In certain cases, each of $Z^7$-$Z^9$ is $CR^{49}$ and each $R^{49}$ is H.

In certain instances of the formula described herein, $R^3$ is of the following structure:

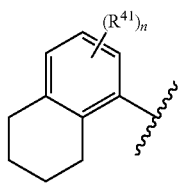

wherein:
n is 1-3; and
each $R^{41}$ is independently selected from H, alkyl, substituted alkyl, aryl, substituted aryl, heteroaryl, substituted heteroaryl, alkoxy, substituted alkoxy, halogen, nitro, cyano, hydroxy, —$NH_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino. In certain cases, each $R^{41}$ is H.

In certain instances of the formula described herein, $R^3$ is of the following structure:

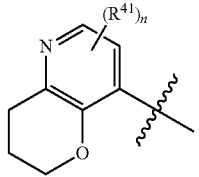

wherein:

n is 1-2; and each $R^{41}$ is independently selected from H, alkyl, substituted alkyl, aryl, substituted aryl, heteroaryl, substituted heteroaryl, alkoxy, substituted alkoxy, halogen, nitro, cyano, hydroxy, —NH$_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino. In certain cases, each $R^{41}$ is H.

In certain instances of the formula described herein, $R^a$ is of the following structure:

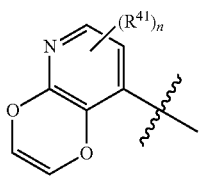

wherein:

n is 1-2; and each $R^{41}$ is independently selected from H, alkyl, substituted alkyl, aryl, substituted aryl, heteroaryl, substituted heteroaryl, alkoxy, substituted alkoxy, halogen, nitro, cyano, hydroxy, —NH$_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino. In certain cases, each $R^{41}$ is H.

In certain instances of the formula described herein, $R^a$ is of the following structure:

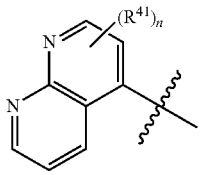

wherein:

n is 1-2; and each $R^{41}$ is independently selected from H, alkyl, substituted alkyl, aryl, substituted aryl, heteroaryl, substituted heteroaryl, alkoxy, substituted alkoxy, halogen, nitro, cyano, hydroxy, —NH$_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino. In certain cases, each $R^{41}$ is H.

In certain instances of the formula described herein, $R^3$ is of the following structure:

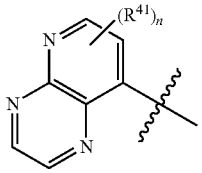

wherein:

n is 1-2; and each $R^{41}$ is independently selected from H, alkyl, substituted alkyl, aryl, substituted aryl, heteroaryl, substituted heteroaryl, alkoxy, substituted alkoxy, halogen, nitro, cyano, hydroxy, —NH$_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino. In certain cases, each $R^{41}$ is H.

In certain instances of the formula described herein, $R^3$ is of the following structure:

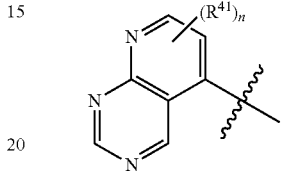

wherein:

n is 1-2; and each $R^{41}$ is independently selected from H, alkyl, substituted alkyl, aryl, substituted aryl, heteroaryl, substituted heteroaryl, alkoxy, substituted alkoxy, halogen, nitro, cyano, hydroxy, —NH$_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino. In certain cases, each $R^{41}$ is H.

In certain instances of the formula n is of the following structure:

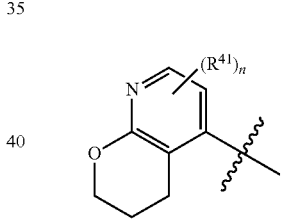

wherein:

n is 1-2; and each $R^{41}$ is independently selected from H, alkyl, substituted alkyl, aryl, substituted aryl, heteroaryl, substituted heteroaryl, alkoxy, substituted alkoxy, halogen, nitro, cyano, hydroxy, —NH$_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino. In certain cases, each $R^{41}$ is H.

In certain instances of the formula described herein, $R^3$ is of the following structure:

wherein:

n is 1-2; and each $R^{41}$ is independently selected from H, alkyl, substituted alkyl, aryl, substituted aryl, heteroaryl, substituted heteroaryl, alkoxy, substituted alkoxy, halogen, nitro, cyano, hydroxy, —NH₂, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino. In certain cases, each $R^{41}$ is H.

In certain embodiments, the subject compound is of one of the following structures in Table 1B:

| Compound No. | Structure |
|---|---|
| 1B | 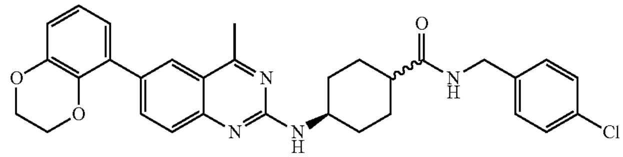 |
| 2B | 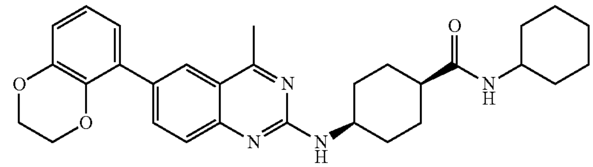 [SMILES: Cc1nc(N[C@H]2CC[C@@H](C(=O)NC3CCCCC3)CC2)nc2ccc(-c3cccc4c3OCCO4)cc12] |
| 3B | 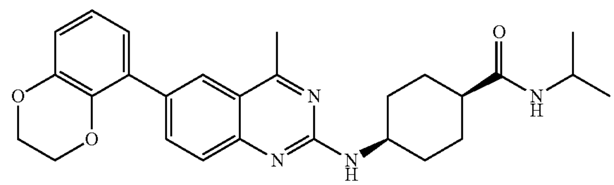 [SMILES: Cc1nc(N[C@H]2CC[C@@H](C(=O)NC(C)C)CC2)nc2ccc(-c3cccc4c3OCCO4)cc12] |
| 4B | 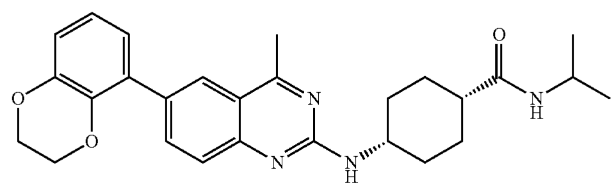 [SMILES: Cc1nc(N[C@H]2CC[C@@H](C(=O)NC(C)C)CC2)nc2ccc(-c3cccc4c3OCCO4)cc12] |
| 5B | 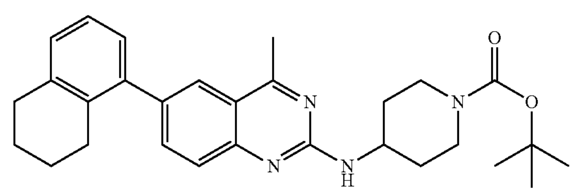 [SMILES: Cc1nc(NC2CCN(C(=O)OC(C)(C)C)CC2)nc2ccc(-c3cccc4c3CCCC4)cc12] |
| 6B | 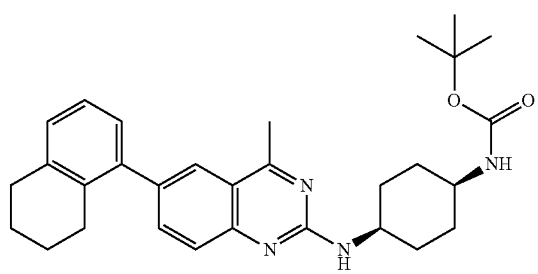 [SMILES: Cc1nc(N[C@H]2CC[C@@H](NC(=O)OC(C)(C)C)CC2)nc2ccc(-c3cccc4c3CCCC4)cc12] |
| 7B | 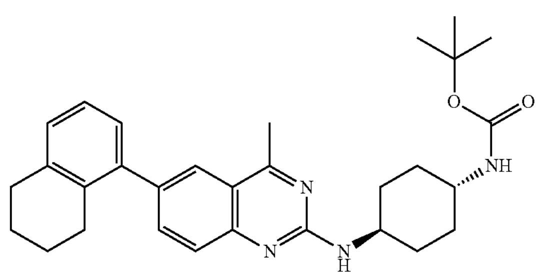 [SMILES: Cc1nc(N[C@H]2CC[C@H](NC(=O)OC(C)(C)C)CC2)nc2ccc(-c3cccc4c3CCCC4)cc12] |

-continued
| Compound No. | Structure |
|---|---|
| 8B | 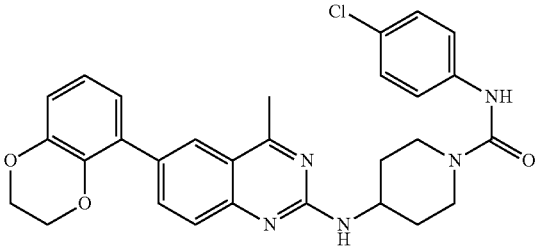 [SMILES: Cc1nc(NC2CCN(C(=O)Nc3ccc(Cl)cc3)CC2)nc2ccc(-c3cccc4c3OCCO4)cc12] |
| 9B | 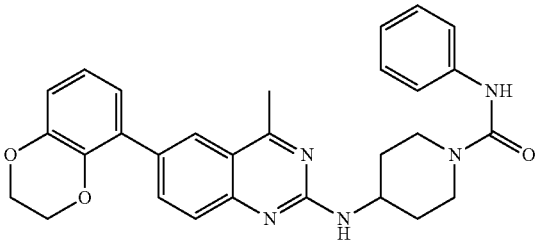 [SMILES: Cc1nc(NC2CCN(C(=O)Nc3ccccc3)CC2)nc2ccc(-c3cccc4c3OCCO4)cc12] |
In certain embodiments, the subject compound is of one of the following structures in Table 1C:
| Compound No. | Structure |
|---|---|
| 1C | 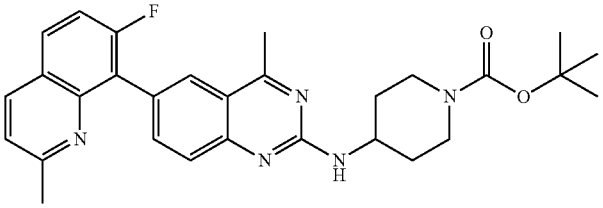 |
| 2C | 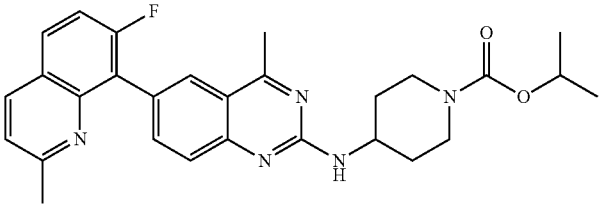 [SMILES: Cc1ccc2ccc(F)c(-c3ccc4nc(NC5CCN(C(=O)OC(C)C)CC5)nc(C)c4c3)c2n1] |
| 3C | 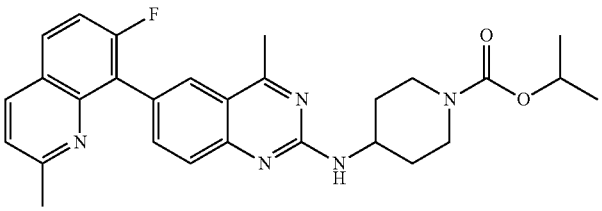 [SMILES: Cc1ccc2ccc(F)c(-c3ccc4nc(NC5CCN(C(=O)OC(C)C)CC5)nc(C)c4c3)c2n1] |
| 4C | 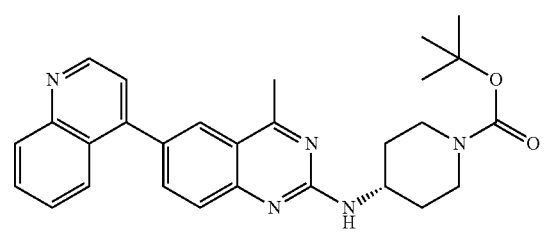 |

-continued
| Compound No. | Structure |
|---|---|
| 5C | 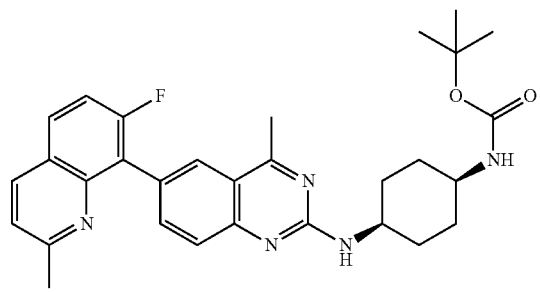 [SMILES: Cc1ccc2ccc(F)c(-c3ccc4nc(N[C@H]5CC[C@@H](NC(=O)OC(C)(C)C)CC5)nc(C)c4c3)c2n1] |
| 6C | 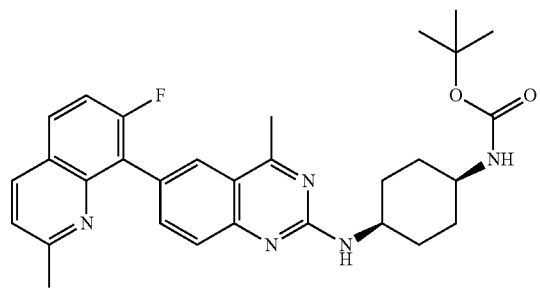 [SMILES: Cc1ccc2ccc(F)c(-c3ccc4nc(N[C@H]5CC[C@@H](NC(=O)OC(C)(C)C)CC5)nc(C)c4c3)c2n1] |
| 7C | 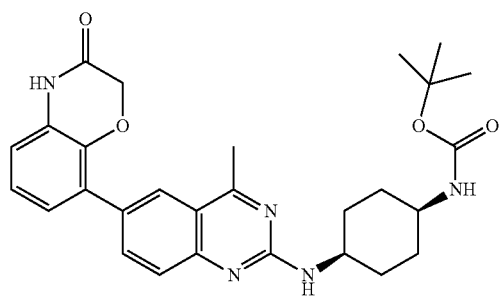 [SMILES: Cc1nc(N[C@H]2CC[C@@H](NC(=O)OC(C)(C)C)CC2)nc2ccc(-c3cccc4c3OCC(=O)N4)cc12] |
| 8C | 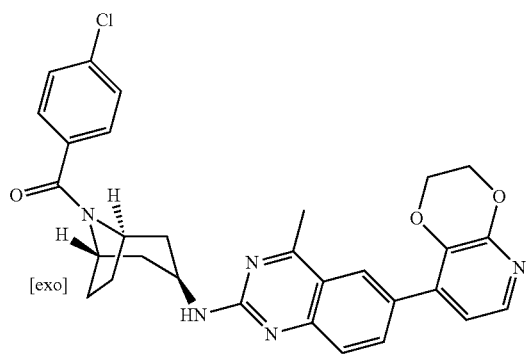 [SMILES: Cc1nc(N[C@@H]2C[C@H]3CC[C@@H](C2)N3C(=O)c2ccc(Cl)cc2)nc2ccc(-c3ccnc4c3OCCO4)cc12] |
| 9C | 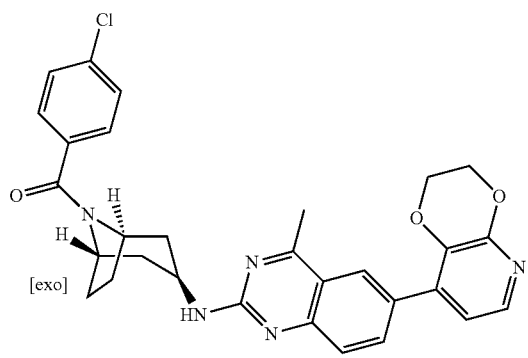 [SMILES: Cc1nc(N[C@@H]2C[C@H]3CC[C@@H](C2)N3C(=O)c2ccc(Cl)cc2)nc2ccc(-c3ccnc4c3OCCO4)cc12] |

-continued

| Compound No. | Structure |
|---|---|
| 10C | [structure: 6-bromo-4-methylquinazolin-2-yl with N-methyl-N-(1-Boc-piperidin-4-yl)amino substituent] |
| 11C | [structure: 4-methyl-6-(7-fluoro-2-methylquinolin-8-yl)quinazolin-2-yl with N-methyl-N-(1-Boc-piperidin-4-yl)amino substituent] |

In certain embodiments, the subject compound is of one of the following structures in Table 1D:

| Compound No. | Structure |
|---|---|
| 1D | [structure: 6-(2,3-dihydro-[1,4]dioxino[2,3-b]pyridin-8-yl)-5-fluoro-4-methylquinazolin-2-yl with NH-bicyclo[2.2.2]octyl-NH-Boc] |
| 2D | [structure: 6-(2,3-dihydro-[1,4]dioxino[2,3-b]pyridin-8-yl)-8-fluoro-4-methylquinazolin-2-yl with NH-bicyclo[2.2.2]octyl-NH-Boc] |
| 3D | [structure: 6-(2,3-dihydro-[1,4]dioxino[2,3-b]pyridin-8-yl)-4-methylquinazolin-2-yl with NH-bicyclo[2.2.2]octyl-NH-C(O)-isoxazol-3-yl] |

-continued
| Compound No. | Structure |
|---|---|
| 4D | 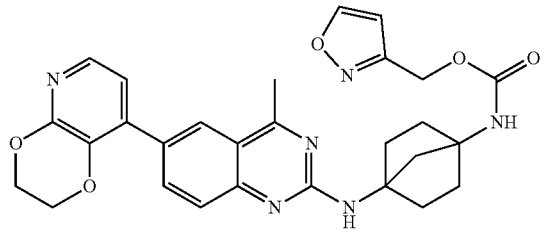 [SMILES: Cc1nc(NC23CCC(NC(=O)OCc4ccon4)(CC2)C3)nc2ccc(-c3ccnc4c3OCCO4)cc12] |
| 5D | 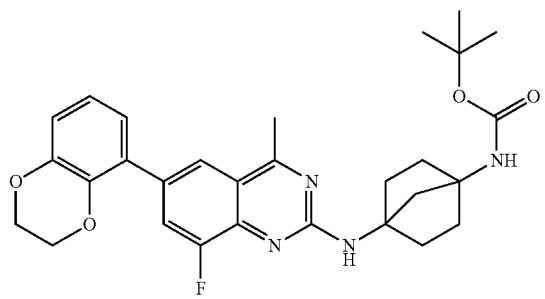 [SMILES: Cc1nc(NC23CCC(NC(=O)OC(C)(C)C)(CC2)C3)nc2c(F)cc(-c3cccc4c3OCCO4)cc12] |
| 6D | 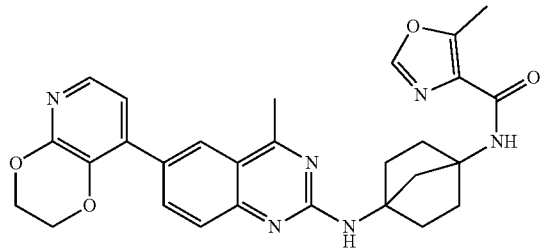 [SMILES: Cc1ocnc1C(=O)NC12CCC(Nc3nc(C)c4cc(-c5ccnc6c5OCCO6)ccc4n3)(CC1)C2] |
| 7D | 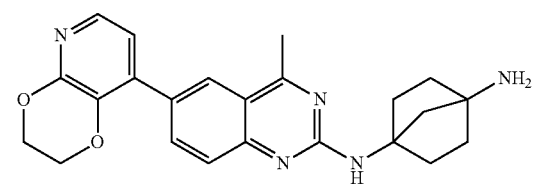 [SMILES: Cc1nc(NC23CCC(N)(CC2)C3)nc2ccc(-c3ccnc4c3OCCO4)cc12] |
| 8D | 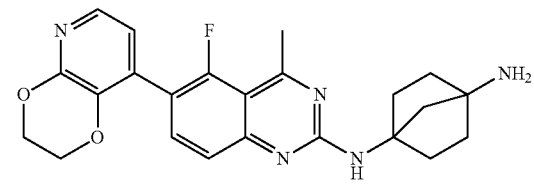 [SMILES: Cc1nc(NC23CCC(N)(CC2)C3)nc2ccc(-c3ccnc4c3OCCO4)c(F)c12] |
| 9D | 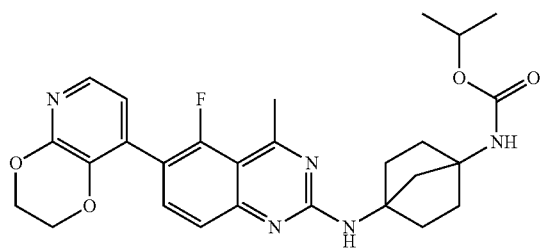 [SMILES: Cc1nc(NC23CCC(NC(=O)OC(C)C)(CC2)C3)nc2ccc(-c3ccnc4c3OCCO4)c(F)c12] |

| Compound No. | Structure |
|---|---|
| 10D | 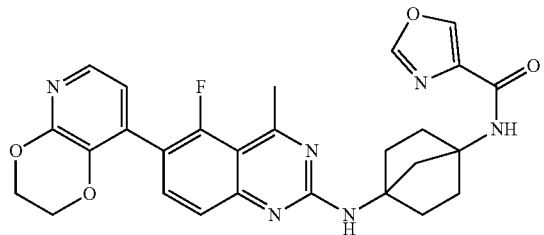 [SMILES: Cc1nc(NC23CCC(NC(=O)c4cocn4)(CC2)C3)nc2ccc(-c3ccnc4c3OCCO4)c(F)c12] |
| 11D | 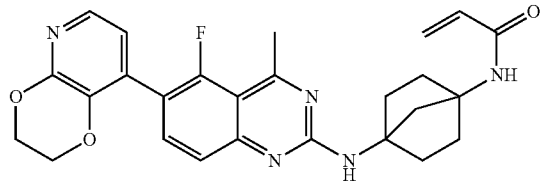 [SMILES: C=CC(=O)NC12CCC(Nc3nc(C)c4c(F)c(-c5ccnc6c5OCCO6)ccc4n3)(CC1)C2] |
| 12D | 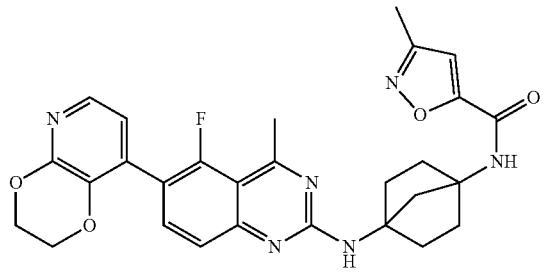 [SMILES: Cc1cc(C(=O)NC23CCC(Nc4nc(C)c5c(F)c(-c6ccnc7c6OCCO7)ccc5n4)(CC2)C3)on1] |
| 13D | 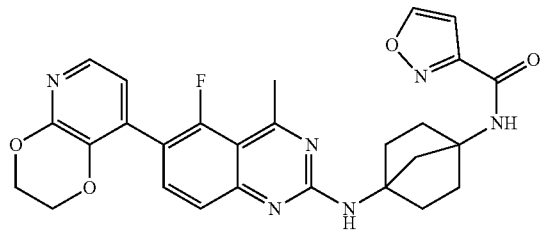 [SMILES: Cc1nc(NC23CCC(NC(=O)c4ccon4)(CC2)C3)nc2ccc(-c3ccnc4c3OCCO4)c(F)c12] |
| 14D | 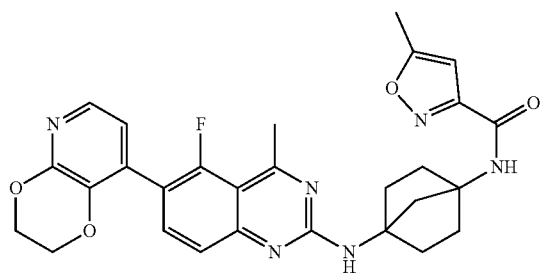 [SMILES: Cc1cc(C(=O)NC23CCC(Nc4nc(C)c5c(F)c(-c6ccnc7c6OCCO7)ccc5n4)(CC2)C3)no1] |
| 15D | 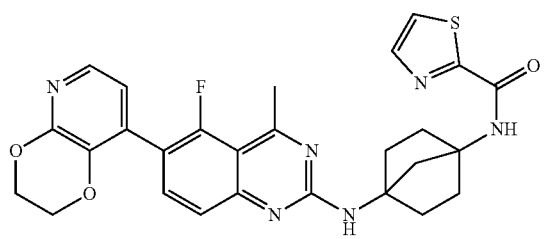 [SMILES: Cc1nc(NC23CCC(NC(=O)c4ncco4)(CC2)C3)nc2ccc(-c3ccnc4c3OCCO4)c(F)c12] |

-continued

| Compound No. | Structure |
|---|---|
| 16D | (structure) |
| 17D | (structure) |
| 18D | (structure) |
| 19D | (structure) |
| 20D | (structure) |
| 21D | (structure) |

-continued

| Compound No. | Structure |
|---|---|
| 22D | 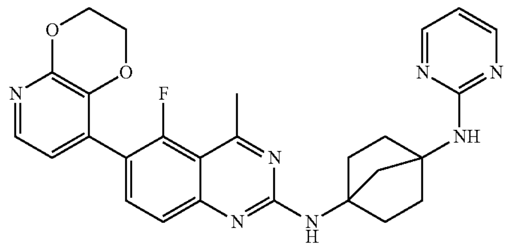 [SMILES: Cc1nc(NC23CCC(Nc4ncccn4)(CC2)C3)nc2ccc(-c3ccnc4c3OCCO4)c(F)c12] |
| 23D | 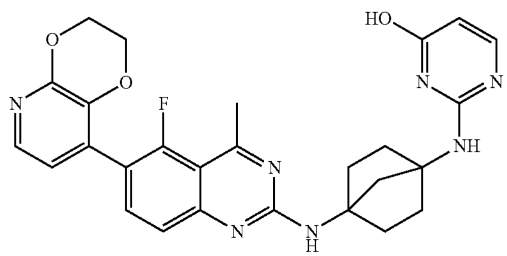 [SMILES: Cc1nc(NC23CCC(Nc4nccc(O)n4)(CC2)C3)nc2ccc(-c3ccnc4c3OCCO4)c(F)c12] |
| 24D | 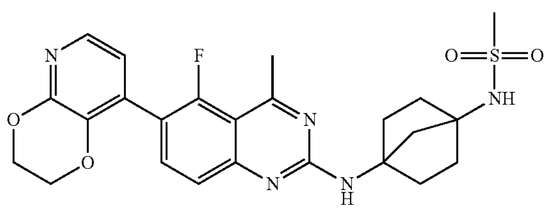 [SMILES: Cc1nc(NC23CCC(NS(C)(=O)=O)(CC2)C3)nc2ccc(-c3ccnc4c3OCCO4)c(F)c12] |
| 25D | 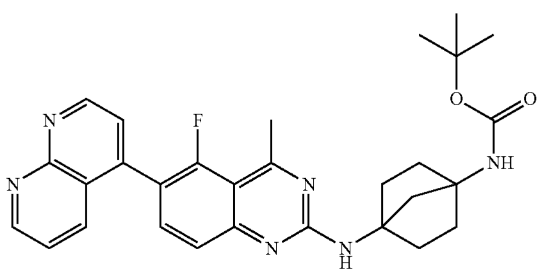 [SMILES: Cc1nc(NC23CCC(NC(=O)OC(C)(C)C)(CC2)C3)nc2ccc(-c3ccnc4ncccc34)c(F)c12] |
| 26D | 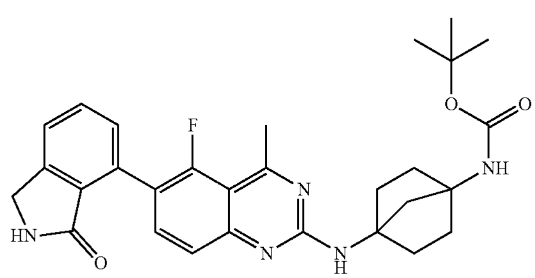 [SMILES: Cc1nc(NC23CCC(NC(=O)OC(C)(C)C)(CC2)C3)nc2ccc(-c3cccc4c3C(=O)NC4)c(F)c12] |
| 27D | 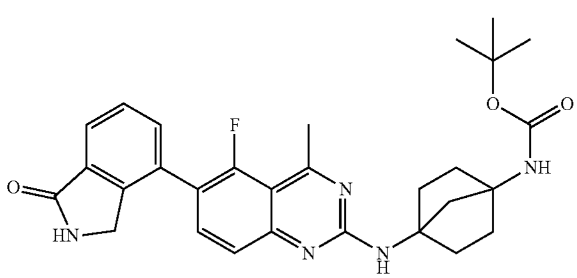 [SMILES: Cc1nc(NC23CCC(NC(=O)OC(C)(C)C)(CC2)C3)nc2ccc(-c3cccc4c3CNC4=O)c(F)c12] |

-continued

| Compound No. | Structure |
|---|---|
| 28D | [chemical structure] |
| 29D | [chemical structure] |
| 30D | [chemical structure] |
| 31D | [chemical structure] |

Aspects of the present disclosure include RAS modulating compounds, salts thereof (e.g., pharmaceutically acceptable salts), and/or solvate, hydrate and/or prodrug forms thereof. In addition, it is understood that, in any compound described herein having one or more chiral centers, if an absolute stereochemistry is not expressly indicated, then each center may independently be of R-configuration or S-configuration or a mixture thereof. It will be appreciated that all permutations of salts, solvates, hydrates, prodrugs and stereoisomers are meant to be encompassed by the present disclosure.

In some embodiments, the subject compounds, or a prodrug form thereof, are provided in the form of pharmaceutically acceptable salts. Compounds containing an amine or nitrogen containing heteroaryl group may be basic in nature and accordingly may react with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

In some embodiments, the subject compounds are provided in a prodrug form. "Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non-enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)).

In some embodiments, the subject compounds, prodrugs, stereoisomers or salts thereof are provided in the form of a solvate (e.g., a hydrate). The term "solvates" as used herein refers to a complex or aggregate formed by one or more molecules of a solute, e.g. a prodrug or a pharmaceutically acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

Pharmaceutical Preparations

Also provided are pharmaceutical preparations. Pharmaceutical preparations are compositions that include a RAS modulating compound (for example one or more of the subject compounds, either alone or in the presence of one or more additional active agents) present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the present disclosure is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used.

When administered to a mammal, the compounds and compositions of the present disclosure and pharmaceutically acceptable vehicles, excipients, or diluents may be sterile. In some instances, an aqueous medium is employed as a vehicle when the subject compound is administered intravenously, such as water, saline solutions, and aqueous dextrose and glycerol solutions.

Pharmaceutical compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. Examples of suitable pharmaceutical vehicles and methods for formulation thereof are described in Remington: The Science and Practice of Pharmacy, Alfonso R. Gennaro ed., Mack Publishing Co. Easton, Pa., 19th ed., 1995, Chapters 86, 87, 88, 91, and 92, incorporated herein by reference. The choice of excipient will be determined in part by the particular compound, as well as by the particular method used to administer the composition. Accordingly, there is a wide variety of suitable formulations of the subject pharmaceutical compositions.

Administration of the subject compounds may be systemic or local. In certain embodiments administration to a mammal will result in systemic release of a compound of the present disclosure (for example, into the bloodstream). Methods of administration may include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In certain embodiments, the compounds and compositions of the present disclosure are administered subcutaneously. In certain embodiments, the compounds and compositions of the present disclosure are administered orally. In certain embodiments, it may be desirable to administer one or more compounds of the present disclosure locally to the area in need of treatment. This may be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A subject compound may also be formulated for oral administration. For an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers. In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

The subject formulations can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

In some embodiments, formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are appropriate. In some embodiments the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (e.g., sun blocking agents), etc.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms of the present disclosure depend on the particular compound employed and the effect to be achieved, and the pharmacodynamics associated with each compound in the host. In pharmaceutical dosage forms, the compounds may be administered in the form of a free base, their pharmaceutically acceptable salts, or they may also be used alone or in appropriate association, as well as in combination, with other pharmaceutically active compounds.

Dose levels can vary as a function of the specific compound, the nature of the delivery vehicle, and the like. Desired dosages for a given compound are readily determinable by a variety of means. The dose administered to an animal, particularly a human, in the context of the present disclosure should be sufficient to affect a prophylactic or therapeutic response in the animal over a reasonable time frame, e.g., as described in greater detail herein. Dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound.

Methods of Inhibiting Mutant RAS

The RAS modulating compounds of the present disclosure find use in modulating the activity of a target RAS in a sample. The target RAS can be a mutant RAS. Aspects of the subject methods include contacting the sample with an effective amount of a RAS modulating compound (e.g., as described herein). In some cases, an effective amount of a RAS modulating compound is an amount sufficient to inhibit the activity of the target RAS in a sample by 10% or more, such as 20% or more, 30% or more, 40% or more, 50% or more, 60% or more, 70% or more, 80% or more, 90% or more, or even more relative to a control, e.g., a sample not contacted with the compound of interest.

As used herein, the term "sample" relates to a material or mixture of materials, in some cases in liquid form, containing one or more analytes of interest. In some embodiments, the term as used in its broadest sense, refers to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents. The term "sample" may also refer to a "biological sample". As used herein, the term "a biological sample" refers to a whole organism or a subset of its tissues, cells or component parts (e.g. body fluids, including, but not limited to, blood, mucus, lymphatic fluid, synovial fluid, cerebrospinal fluid, saliva, amniotic fluid, amniotic cord blood, urine, vaginal fluid and semen). A "biological sample" can also refer to a homogenate, lysate or extract prepared from a whole organism or a subset of its tissues, cells or component parts, or a fraction or portion thereof, including but not limited to, plasma, serum, spinal fluid, lymph fluid, the external sections of the skin, respiratory, intestinal, and genitourinary tracts, tears, saliva, milk, blood cells, tumors and organs. In certain embodiments, the sample has been removed from an animal or plant. Biological samples may include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

In some cases, the target RAS is a mutant kRAS, a mutant nRAS or a mutant hRAS. The mutant RAS may be one that is responsible for a RAS-induced promotion of cell growth or proliferation in the sample. The subject methods can provide for modulation of the interaction of an activated GTP-bound RAS of interest with a RAF family protein. The subject methods can provide for partial or full blockage of the Ras-Raf-MEK-ERK pathway (MAPK pathway) to result in modulation of cell proliferation in a sample. In certain instances, the sample is a cellular sample and the cells are cancer cells of interest (e.g., as described herein). The sample can be in vitro or in vivo. In some instances, the subject methods result in inhibition or decrease of RAS-induced proliferation by 10% or more, such as 20% or more, 30% or more, 40% or more, 50% or more, 60% or more, 70% or more, 80% or more, 90% or more, or even more, relative to a control, e.g., cells not contacted with the compound of interest.

Aspects of the subject methods include evaluating the activity of the target RAS in the sample. As used herein, the terms "evaluating", "determining," "measuring," and "assessing," and "assaying" are used interchangeably and include both quantitative and qualitative determinations. Evaluating the activity of the target RAS can be performed before and/or after the sample is contacted with the subject compound and can be achieved using any convenient methods, including both direct methods (e.g., assays of GTPase activity or inhibition assays of direct binding of the target RAS) and indirect methods (e.g., measuring downstream signals produced by the Ras-Raf-MEK-ERK pathway or measuring cellular proliferation). Exemplary methods for evaluating the activity of the target RAS are described herein, for example, the cytotoxicity assay, the phosphorylated ERK bioassay, the cell morphology assay and the Fly assay of the Examples section.

Methods of Treatment

The RAS modulating compounds of the present disclosure find use in treatment of a condition or disease in a subject in which the activity of a mutant RAS GTPase is implicated (e.g., as described herein). Aspects of the method include administering to a subject in need thereof a therapeutically effective amount of a RAS modulating compound to treat the subject. By "a therapeutically effective amount" is meant the concentration of a compound that is enough to elicit the desired biological effect (e.g., treatment of the condition or disease). By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms. In the context of cancer, the term "treating" includes any or all reducing growth of a solid tumor, inhibiting replication of cancer cells, reducing overall tumor burden, and ameliorating one or more symptoms associated with a cancer.

The subject to be treated can be one that needs of therapy, where the host to be treated is one amenable to treatment using the RAS modulating compound. In some embodiments, the subject is one that has kRAS-driven cancer. In certain embodiments, the subject has a tumor with cells containing a kRAS G12V mutation. In some embodiments, the subject is one that has a hRAS-driven tumor. In some embodiments, the subject is one that has a nRAS-driven tumor. In another aspect, the subject is a child with one of many genetic conditions termed RASopathies, as described by Niemeyer CM (RAS diseases in children. Haematologica. 2014; 99:1653-62).

In some cases, the subject methods of treatment include a step of determining or diagnosing whether the subject has a disease associated with a mutant RAS GTPase. The determining step can be performed using any convenient methods. In some cases, the determining step includes obtaining a biological sample from the subject and assaying the sample for the presence of a mutant RAS. The sample can be a cellular sample. In some cases, the sample is a biopsy (e.g., a tumor biopsy). The determining step can include identification of cancer cells including a kRAS mutation. The determining step can include identification of cancer cells including a hRAS mutation. The determining step can include identification of cancer cells including a nRAS mutation. In certain cases, the subject has a MYH associated polyposis, and the determining step includes identifying cells that include a mutant hRAS or nRAS.

Accordingly, a variety of subjects may be amenable to treatment using the RAS modulating compounds and pharmaceutical compositions disclosed herein. As used herein, the terms "subject" and "host" are used interchangeably. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of RAS modulating compound administered can be determined using any convenient methods to be an amount enough to produce the desired effect in association with a pharmaceutically acceptable diluent, carrier or vehicle. The specifications for the unit dosage forms of the present disclosure will depend on the particular compound employed and the effect to be achieved, and the pharmacodynamics associated with each compound in the host.

In some embodiments, an effective amount of RAS modulating compound is an amount that ranges from about 50 ng/ml to about 50 µg/ml (e.g., from about 50 ng/ml to about 40 µg/ml, from about 30 ng/ml to about 20 µg/ml, from about 50 ng/ml to about 10 µg/ml, from about 50 ng/ml to about 1 µg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, an effective amount of a RAS modulating compound is an amount that ranges from about 10 pg to about 100 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 µg, from about 1 µg to about 10 µg, from about 10 µg to about 50 µg, from about 50 µg to about 150 µg, from about 150 µg to about 250 µg, from about 250 µg to about 500 µg, from about 500 µg to about 750 µg, from about 750 µg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg.

In some embodiments, a single dose of the subject compound is administered. In other embodiments, multiple doses of the subject compound are administered. Where multiple doses are administered over a period of time, the RAS modulating compound is administered twice daily (qid), daily (qd), every other day (qod), every third day, three times per week (tiw), or twice per week (biw) over a period of time. For example, a compound is administered qid, qd, qod, tiw, or biw over a period of from one day to about 2 years or more. For example, a compound is administered at any of the aforementioned frequencies for one week, two weeks, one month, two months, six months, one year, or two years, or more, depending on various factors.

Any of a variety of methods can be used to determine whether a treatment method is effective. For example, a biological sample obtained from an individual who has been treated with a subject method can be assayed for the presence and/or level of cells including a target RAS. Assessment of the effectiveness of the methods of treatment on the subject can include assessment of the subject before, during and/or after treatment, using any convenient methods. Aspects of the subject methods further include a step of assessing the therapeutic response of the subject to the treatment.

In some embodiments, the method includes assessing the condition of the subject, including diagnosing or assessing one or more symptoms of the subject which are associated with the disease or condition of interest being treated (e.g., as described herein). In some embodiments, the method includes obtaining a biological sample from the subject and assaying the sample, e.g., for the presence of a mutant RAS or for the presence of cells that are associated with the disease or condition of interest (e.g., as described herein). The sample can be a cellular sample. In some cases, the sample is a biopsy. The assessment step(s) of the subject method can be performed at one or more times before, during and/or after administration of the subject compounds, using any convenient methods. In certain cases, the assessment step includes identification of cancer cells including a kRAS mutation. The determining step can include identification of cancer cells including a hRAS mutation. In certain instances, assessing the subject include diagnosing whether the subject has a MYH associated polyposis. In certain cases, assessing the subject includes identifying cells that include a mutant hRAS or nRAS.

Combination Therapy

Aspects of the present disclosure further include combination therapies. In certain embodiments, the subject method includes administering a therapeutically effective amount of one or more additional active agents. By combination therapy is meant that a RAS modulating compound (e.g., as described herein) can be used in a combination with another therapeutic agent to treat a single disease or condition. In particular embodiments, a compound of the present disclosure is administered concurrently with the administration of another therapeutic agent, which can be administered as a component of a composition including the compound of the present disclosure or as a component of a different composition. In certain embodiments, a composition including a compound of the present disclosure is administered prior or after administration of another therapeutic agent.

The subject compounds can be administered in combination with other therapeutic agents in a variety of therapeutic applications. Therapeutic applications of interest for combination therapy include those applications in which activity of a mutant RAS is the cause or a compounding factor in disease progression. As such, the subject compounds find use in combination therapies in which the inhibition of a target RAS in the subject is desired. Examples of disease conditions which may be treated by a combination therapy including a subject compound include, but are not limited to, cancer and MYH associated polyposis.

The subject RAS modulating compounds can be used jointly with any agent useful in the treatment of a neoplastic condition, such as anti-cancer agents and anti-tumor agents. One class of anti-cancer agents of interest includes chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation.

Agents of interest which can be used in jointly with the subject RAS modulating compounds include, but are not limited to, Cancer chemotherapeutic agents, Agents that act to reduce cellular proliferation, Antimetabolite agents, Microtubule affecting agents, Hormone modulators and steroids, natural products and Biological response modifiers, e.g., as described in greater detail below.

Cancer chemotherapeutic agents include non-peptidic (i.e., non-proteinaceous) compounds that reduce proliferation of cancer cells and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones. Peptidic compounds can also be used. Suitable cancer chemotherapeutic agents include dolastatin and active analogs and derivatives thereof; and auristatin and active analogs and derivatives thereof (e.g., Monomethyl auristatin D (MMAD), monomethyl auristatin E (MMAE), monomethyl auristatin F (MMAF), and the like). See, e.g., WO 96/33212, WO 96/14856, and U.S. Pat. No. 6,323,315. For example, dolastatin 10 or auristatin PE can be included in an antibody-drug conjugate of the present disclosure. Suitable cancer chemotherapeutic agents also include maytansinoids and active analogs and derivatives thereof (see, e.g., EP 1391213; and Liu et al (1996) Proc. Natl. Acad. Sci. USA 93:8618-8623); duocarmycins and active analogs and derivatives thereof (e.g., including the synthetic analogues, KW-2189 and CB 1-TM1); and benzodiazepines and active analogs and derivatives thereof (e.g., pyrrolobenzodiazepine (PBD).

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine. Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, epothilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation. Therefore, compounds that bind to the estrogen receptor are used to block this activity. Corticosteroids may inhibit T cell proliferation.

Other suitable chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporne, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

Taxanes are suitable for use. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St Louis, Mo. (T7402 from *Taxus brevifolia*; or T-1912 from *Taxus yannanensis*). Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose). Also included within the term "taxane" are a variety of known derivatives, including both hydrophilic derivatives, and hydrophobic derivatives. Taxane derivatives include, but are not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ; (8) colony-stimulating factors; and (9) inhibitors of angiogenesis.

Utility

The RAS modulating compounds, e.g., as described herein, find use in a variety of applications. Applications of interest include but are not limited to: therapeutic applications and research applications. RAS modulating compounds of the present disclosure and pharmaceutical compositions including the same find use in a variety of therapeutic applications. Therapeutic applications of interest include those applications in which a target RAS GTPase activity is the cause or a compounding factor in disease progression. As such, the subject compounds find use in the treatment of a variety of different conditions in which the modulation of a target RAS in the host is desired. Examples of disease conditions which may be treated with compounds of the invention include, but are not limited to cancer, MYH associated polyposis and RASopathies.

The subject compounds and compositions find use in treatment of a variety of cancers, including but not limited to, pancreatic cancer, colon cancer, endometrial cancer, lung adenocarcinoma, skin cancer, acute myeloid leukemia (AML) and multiple myeloma. In certain instances, the target RAS is a mutated kRAS implicated in pancreatic cancers, colon cancers, endometrial cancers, lung adenocarcinomas, e.g., non-small cell lung carcinoma (NSCLC), skin cancers, acute myeloid leukemia (AML) liquid tumors or a multiple myeloma cancer.

The subject compounds and compositions find use in treatment of MYH associated polyposis, a hereditary condition characterized by a tendency to develop multiple adenomatous colon polyps with a concomitant increased risk of colorectal cancer. In some instances, patients who may be treated according to the subject methods also possess a mutated kRAS gene/protein. The subject compounds and compositions also find use in treatment of a genetic condition termed RASopathy, as described by Niemeyer CM (RAS diseases in children. Haematologica. 2014; 99:1653-62). In such applications, the patient can be one that has a kRAS, hRAS or nRAS mutation, such as a G12V mutation.

The subject compounds find use in a variety of research applications including the identification and testing of candidate RAS modulating compounds (e.g., for pharmaceutical development) and performing research on disease conditions of interest in which the activity of a target RAS GTPase is implicated. Research applications of interest can involve use of the subject compounds in a variety of in vitro assays including high throughput screening assays, potency assays, and competitive inhibition assays where the subject compounds can be useful as a control compound or as a tool in the investigation the pathology of cells of interest.

Systems and Kits

Also provided are kits that include RAS modulating compounds (e.g., as described herein). Systems of the present disclosure include collections of active agents brought together, e.g., by a health care practitioner, for administration to a subject, such as a patient. Such systems may include a RAS modulating compound and one or more additional active agents (e.g., as described herein). Kits that include RAS modulating compounds which are provided that may include one or more dosages of a RAS modulating compound, and optionally one or more dosages of one or more additional active agents. Conveniently, the formulations may be provided in a unit dosage format. In such kits, in addition to the containers containing the formulation(s), e.g. unit doses, is an informational package insert describing the use of the subject formulations in the methods of the invention, e.g., instructions for using the subject unit doses to treat cellular proliferative disease conditions. These instructions may be present in the subject systems and kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following example(s) is/are offered by way of illustration and not by way of limitation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, cells, and kits for methods referred to in, or related to, this disclosure are available from commercial vendors such as BioRad, Agilent Technologies, Thermo Fisher Scientific, Sigma-Aldrich, New England Biolabs (NEB), Takara Bio USA, Inc., and the like, as well as repositories such as e.g., Addgene, Inc., American Type Culture Collection (ATCC), and the like.

Example 1: Activity of Compounds

Cell Proliferation Assays

Compounds are assayed for inhibition of cell proliferation and killing cancer cells. Cytotoxicity assays are conducted according to the following general procedure. SW820 cells (ATCC CCL-227) are maintained in DMEM Low Glucose (Corning 10-014-CV) media supplemented with 10% fetal bovine serum and 1% PenStrep and grown at 37° C. in 5% $CO_2$. Cells are plated into 96 well flat bottom plates (2 million/plate, ~20,000/well, 200 µL media/well). The cells are allowed to settle and adhere to the plate bottom overnight. Compounds are diluted in media from a 10 mM stock solution starting at 50 µM, using 2-fold dilutions, in a column in a 96-well plate. Media is removed from the plate containing cells and replaced with media containing diluted compounds. Plates are incubated 72 hours at 37° C. in 5% $CO_2$. Plates are allowed to come to room temperature and 100 µL CellTiter-Glo 2.0 reagent (Promega, G924C) is added at room temperature. Plates are shaken for 2 minutes, then allowed to stand for 15 minutes. Luminescence is read with FLx800 (BioTek Instruments). Data is plotted with GraphPad Prizm 8.0.

Exemplary KRAS inhibitor compounds and their $IC_{50}$s against SW620 Cell Lines are shown in Table 2.

TABLE 2

IC$_{50s}$ of exemplary KRAS Inhibitors against SW620 Cell Lines

| Compound No. | Structure | SW620 IC$_{50}$ |
|---|---|---|
| 1B | 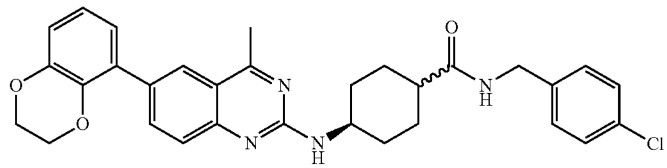 | + |
| 2B | 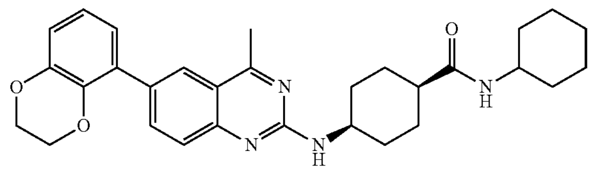 [SMILES: Cc1nc(N[C@H]2CC[C@@H](C(=O)NC3CCCCC3)CC2)nc2ccc(-c3cccc4c3OCCO4)cc12] | + |
| 1C | 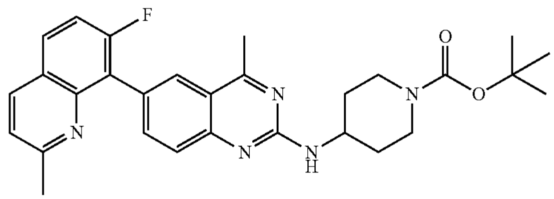 [SMILES: Cc1ccc2ccc(F)c(-c3ccc4nc(NC5CCN(C(=O)OC(C)(C)C)CC5)nc(C)c4c3)c2n1] | ++ |
| 2C | 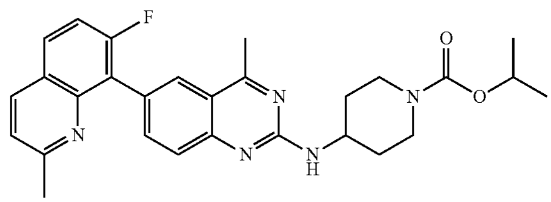 [SMILES: Cc1ccc2ccc(F)c(-c3ccc4nc(NC5CCN(C(=O)OC(C)C)CC5)nc(C)c4c3)c2n1] | + |
| 3C | 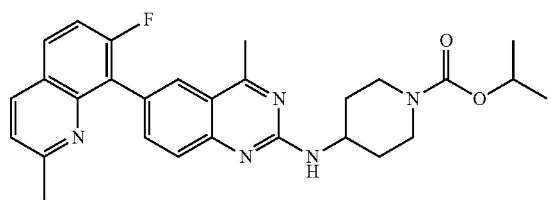 [SMILES: Cc1ccc2ccc(F)c(-c3ccc4nc(NC5CCN(C(=O)OC(C)C)CC5)nc(C)c4c3)c2n1] | + |
| 3B | 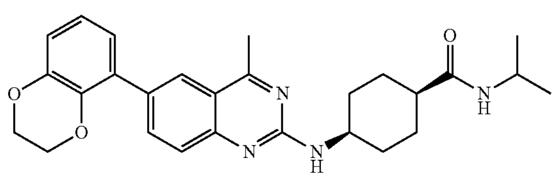 [SMILES: Cc1nc(N[C@H]2CC[C@@H](C(=O)NC(C)C)CC2)nc2ccc(-c3cccc4c3OCCO4)cc12] | + |
| 4B | 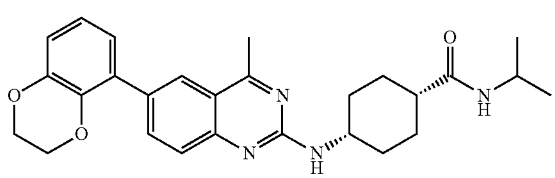 [SMILES: Cc1nc(N[C@H]2CC[C@@H](C(=O)NC(C)C)CC2)nc2ccc(-c3cccc4c3OCCO4)cc12] | + |
| 5B | 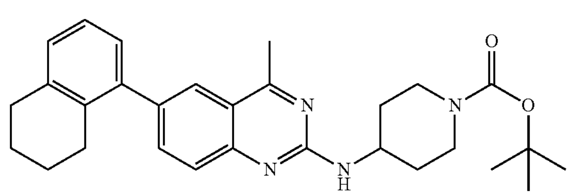 [SMILES: Cc1nc(NC2CCN(C(=O)OC(C)(C)C)CC2)nc2ccc(-c3cccc4c3CCCC4)cc12] | + |

TABLE 2-continued

IC$_{50s}$ of exemplary KRAS Inhibitors against SW620 Cell Lines

| Compound No. | Structure | SW620 IC$_{50}$ |
|---|---|---|
| 4C | 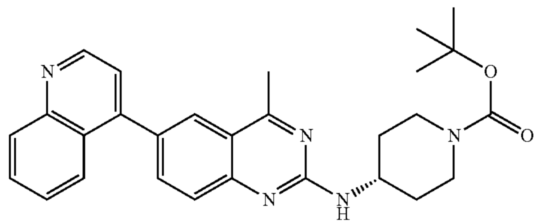 | + |
| 1A | 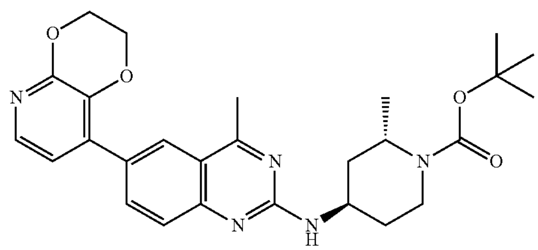 [SMILES: Cc1nc(N[C@@H]2CCN(C(=O)OC(C)(C)C)[C@@H](C)C2)nc2ccc(-c3ccnc4c3OCCO4)cc12] | ++ |
| 2A | 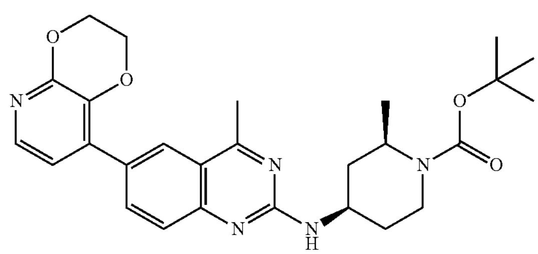 [SMILES: Cc1nc(N[C@@H]2CCN(C(=O)OC(C)(C)C)[C@H](C)C2)nc2ccc(-c3ccnc4c3OCCO4)cc12] | ++ |
| 6B | 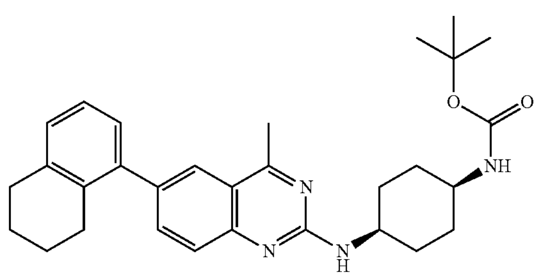 [SMILES: Cc1nc(N[C@H]2CC[C@@H](NC(=O)OC(C)(C)C)CC2)nc2ccc(-c3cccc4c3CCCC4)cc12] | + |
| 7B | 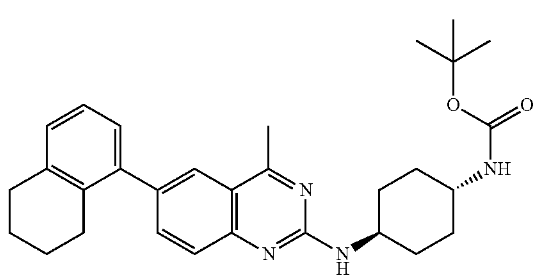 [SMILES: Cc1nc(N[C@H]2CC[C@H](NC(=O)OC(C)(C)C)CC2)nc2ccc(-c3cccc4c3CCCC4)cc12] | + |

TABLE 2-continued

IC$_{50s}$ of exemplary KRAS Inhibitors against SW620 Cell Lines

| Compound No. | Structure | SW620 IC$_{50}$ |
| --- | --- | --- |
| 5C | 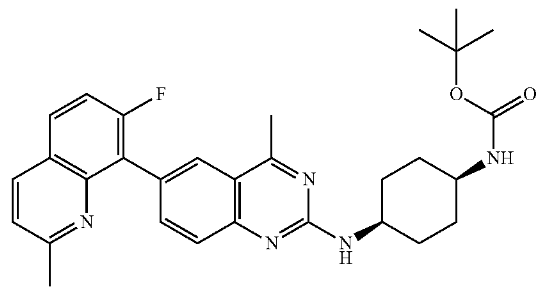 [SMILES: Cc1ccc2ccc(F)c(-c3ccc4nc(N[C@H]5CC[C@@H](NC(=O)OC(C)(C)C)CC5)nc(C)c4c3)c2n1] | + |
| 6C | 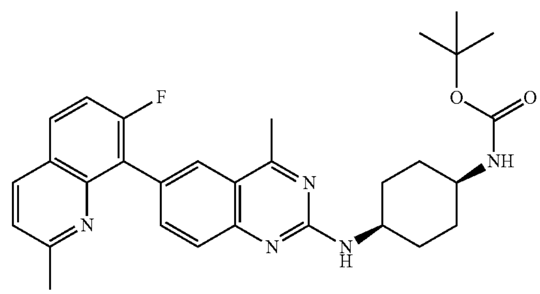 [SMILES: Cc1ccc2ccc(F)c(-c3ccc4nc(N[C@H]5CC[C@@H](NC(=O)OC(C)(C)C)CC5)nc(C)c4c3)c2n1] | + |
| 3A | 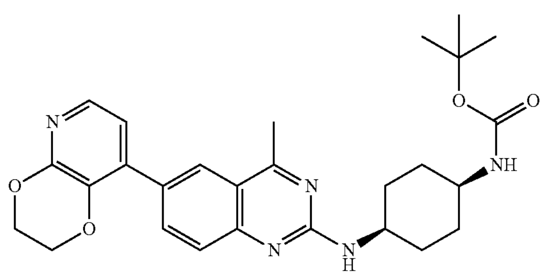 [SMILES: Cc1nc(N[C@H]2CC[C@@H](NC(=O)OC(C)(C)C)CC2)nc2ccc(-c3ccnc4c3OCCO4)cc12] | ++ |
| 4A | 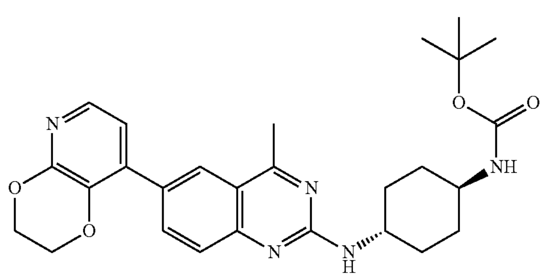 [SMILES: Cc1nc(N[C@H]2CC[C@H](NC(=O)OC(C)(C)C)CC2)nc2ccc(-c3ccnc4c3OCCO4)cc12] | ++ |
| 5A | 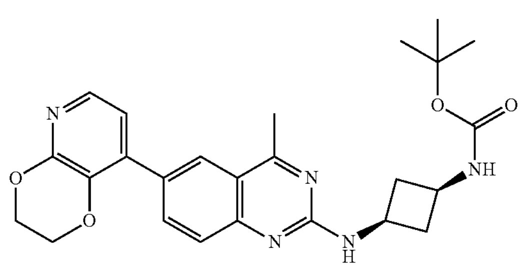 [SMILES: Cc1nc(N[C@H]2C[C@@H](NC(=O)OC(C)(C)C)C2)nc2ccc(-c3ccnc4c3OCCO4)cc12] | ++ |

TABLE 2-continued

IC$_{50s}$ of exemplary KRAS Inhibitors against SW620 Cell Lines

| Compound No. | Structure | SW620 IC$_{50}$ |
| --- | --- | --- |
| 6A | 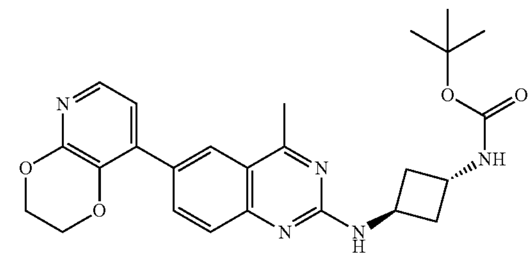 [SMILES: Cc1nc(N[C@H]2C[C@H](NC(=O)OC(C)(C)C)C2)nc2ccc(-c3ccnc4c3OCCO4)cc12] | ++ |
| 7A | 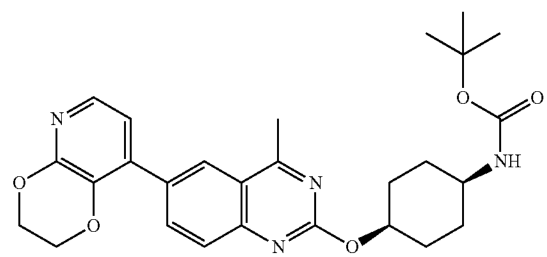 [SMILES: Cc1nc(O[C@H]2CC[C@@H](NC(=O)OC(C)(C)C)CC2)nc2ccc(-c3ccnc4c3OCCO4)cc12] | ++ |
| 8A | 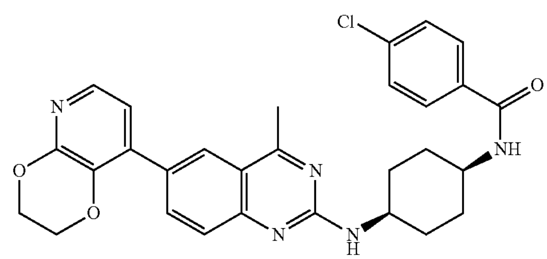 [SMILES: Cc1nc(N[C@H]2CC[C@@H](NC(=O)c3ccc(Cl)cc3)CC2)nc2ccc(-c3ccnc4c3OCCO4)cc12] | ++ |
| 7C | 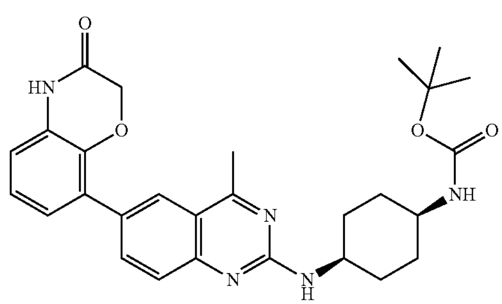 [SMILES: Cc1nc(N[C@H]2CC[C@@H](NC(=O)OC(C)(C)C)CC2)nc2ccc(-c3cccc4c3OCC(=O)N4)cc12] | + |
| 9A | 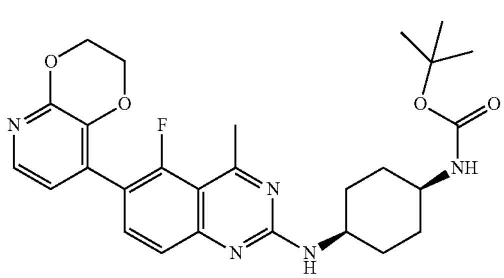 [SMILES: Cc1nc(N[C@H]2CC[C@@H](NC(=O)OC(C)(C)C)CC2)nc2ccc(-c3ccnc4c3OCCO4)c(F)c12] | ++ |

TABLE 2-continued

IC$_{50}$s of exemplary KRAS Inhibitors against SW620 Cell Lines

| Compound No. | Structure | SW620 IC$_{50}$ |
|---|---|---|
| 10A | 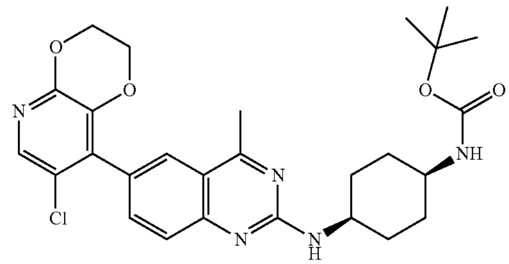 [SMILES: Cc1nc(N[C@H]2CC[C@@H](NC(=O)OC(C)(C)C)CC2)nc2ccc(-c3c(Cl)cnc4c3OCCO4)cc12] | ++ |
| 11A | 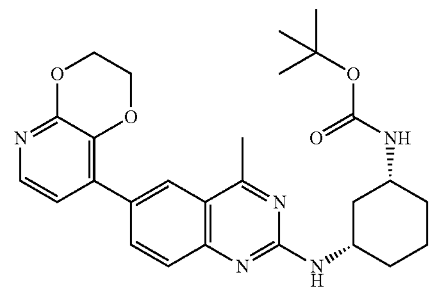 [SMILES: Cc1nc(N[C@H]2CCC[C@@H](NC(=O)OC(C)(C)C)C2)nc2ccc(-c3ccnc4c3OCCO4)cc12] | ++ |
| 12A | 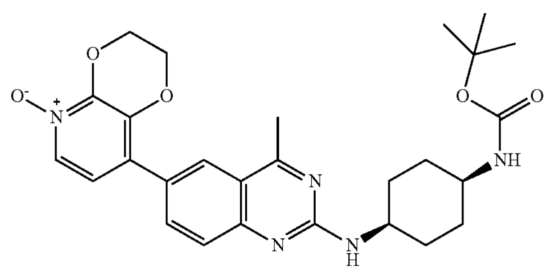 [SMILES: Cc1nc(N[C@H]2CC[C@@H](NC(=O)OC(C)(C)C)CC2)nc2ccc(-c3cc[n+]([O-])c4c3OCCO4)cc12] | + |
| 13A | 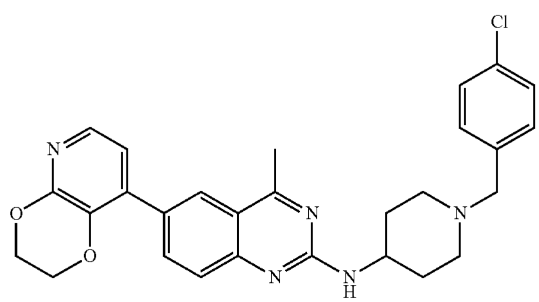 [SMILES: Cc1nc(NC2CCN(Cc3ccc(Cl)cc3)CC2)nc2ccc(-c3ccnc4c3OCCO4)cc12] | ++ |
| 14A | 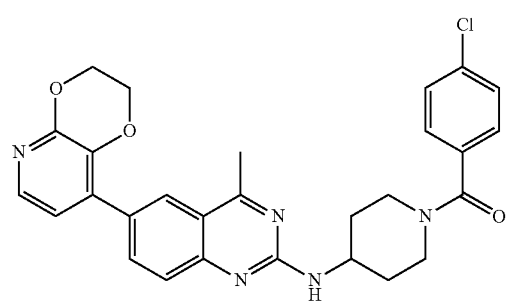 [SMILES: Cc1nc(NC2CCN(C(=O)c3ccc(Cl)cc3)CC2)nc2ccc(-c3ccnc4c3OCCO4)cc12] | ++ |

TABLE 2-continued

IC$_{50s}$ of exemplary KRAS Inhibitors against SW620 Cell Lines

| Compound No. | Structure | SW620 IC$_{50}$ |
| --- | --- | --- |
| 15A | 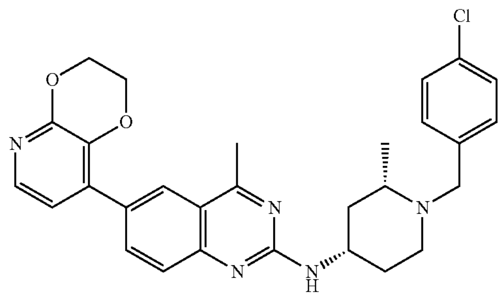 [SMILES: Cc1nc(N[C@H]2CCN(Cc3ccc(Cl)cc3)[C@@H](C)C2)nc2ccc(-c3ccnc4c3OCCO4)cc12] | ++ |
| 16A | 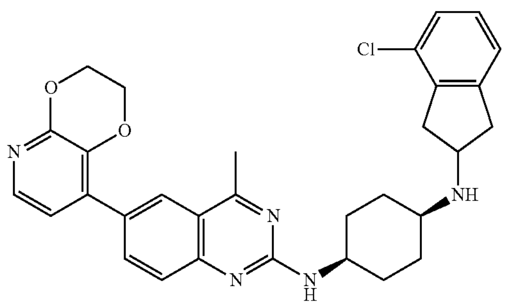 [SMILES: Cc1nc(N[C@H]2CC[C@@H](NC3Cc4cccc(Cl)c4C3)CC2)nc2ccc(-c3ccnc4c3OCCO4)cc12] | ++ |
| 8C | 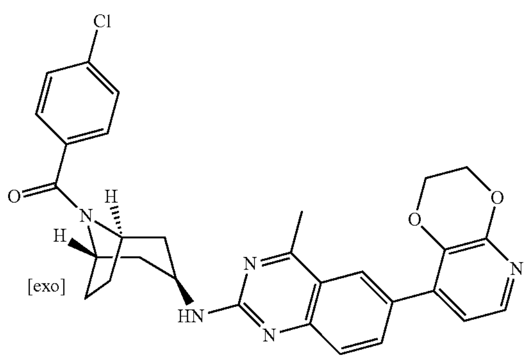 [SMILES: Cc1nc(N[C@@H]2C[C@H]3CC[C@@H](C2)N3C(=O)c2ccc(Cl)cc2)nc2ccc(-c3ccnc4c3OCCO4)cc12] | ++ |
| 9C | 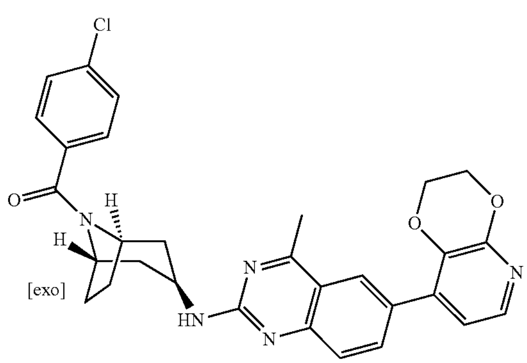 [SMILES: Cc1nc(N[C@@H]2C[C@H]3CC[C@@H](C2)N3C(=O)c2ccc(Cl)cc2)nc2ccc(-c3ccnc4c3OCCO4)cc12] | ++ |

+ = 5-10 μM
++ = less than 5 μM

Example 2: Synthesis of Compounds

Compounds may be synthesized using any convenient method. Methods which can be adapted to prepare compounds of this disclosure includes those methods described by Ungashe et al. in PCT application No. PCT/US2020/027985, filed Apr. 13, 2020, the disclosure of which is herein incorporated by reference in its entirety. Many general references providing commonly known chemical synthetic schemes and conditions useful for synthesizing the disclosed compounds are also available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978). Reactions may be monitored by thin layer chromatography (TLC), LC/MS and reaction products characterized by LC/MS and $^1$H NMR. Intermediates and final products may be purified by silica gel chromatography or by HPLC.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A method of modulating the activity of a target RAS in a sample, the method comprising:
   contacting the sample comprising a target RAS with an effective amount of a RAS modulating compound to modulate the activity of the target RAS, wherein the RAS modulating compound is a compound of formula (I):

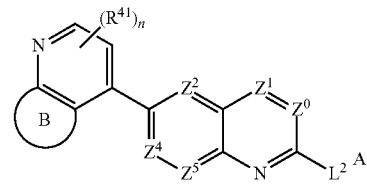

wherein:
A is a monocyclic or bicyclic group selected from heteroaryl, substituted heteroaryl, heterocycle, substituted heterocycle, cycloalkyl and substituted cycloalkyl;
wherein if A is a substituted heterocycle then A is substituted with one or more groups selected from aryl, substituted aryl, carboxy, substituted carboxy, alkylsulfonyl, substituted alkylsulfonyl, alkanoyl, and substituted alkanoyl;
ring B is a cyclic group selected from aryl, substituted aryl, cycloalkyl, substituted cycloalkyl, heteroaryl, substituted heteroaryl, heterocycle, and substituted heterocycle;
$Z^0$ is N or $CR^0$;
$Z^1$ is N or $CR^1$;
$Z^2$ is N or $CR^2$;
$Z^4$ is N or $CR^4$;
$Z^5$ is N or $CR^5$;
$L^2$ is a covalent bond, a linker having a backbone of 1-4 atoms in length, or an optionally substituted non-aromatic heterocycle;
$R^0$-$R^2$ and $R^4$-$R^5$ are independently selected from H, alkyl, substituted alkyl, aryl, substituted aryl, heteroaryl, substituted heteroaryl, alkoxy, substituted alkoxy, halogen, nitro, cyano, hydroxy, —NH$_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino;
each $R^{41}$ is independently selected from H, alkyl, substituted alkyl, aryl, substituted aryl, heteroaryl, substituted heteroaryl, alkoxy, substituted alkoxy, halogen, nitro, cyano, hydroxy, —NH$_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino; and
n is 1-2;
or a salt thereof, or a solvate, hydrate or prodrug form thereof.

2. The method according to claim 1, wherein the sample is a cellular sample.

3. The method according to claim 1, wherein the sample is in vitro.

4. The method according to claim 1, wherein the sample is in vivo.

5. A method of treating a subject for a RAS driven disease, the method comprising:
   administering to the subject a therapeutically effective amount of a RAS modulating compound is a compound of formula (I):

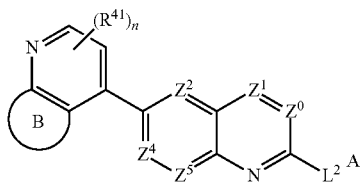

(I)

wherein:
A is a monocyclic or bicyclic group selected from heteroaryl, substituted heteroaryl, heterocycle, substituted heterocycle, cycloalkyl and substituted cycloalkyl;
wherein if A is a substituted heterocycle then A is substituted with one or more groups selected from aryl, substituted aryl, carboxy, substituted carboxy, alkylsulfonyl, substituted alkylsulfonyl, alkanoyl, and substituted alkanoyl;
ring B is a cyclic group selected from aryl, substituted aryl, cycloalkyl, substituted cycloalkyl, heteroaryl, substituted heteroaryl, heterocycle, and substituted heterocycle;
$Z^0$ is N or $CR^0$;
$Z^1$ is N or $CR^1$;
$Z^2$ is N or $CR^2$;
$Z^4$ is N or $CR^4$;
$Z^5$ is N or $CR^5$;
$L^2$ is a covalent bond, a linker having a backbone of 1-4 atoms in length, or an optionally substituted non-aromatic heterocycle;
$R^0$, $R^2$, and $R^4$-$R^5$ are independently selected from H, alkyl, substituted alkyl, aryl, substituted aryl, heteroaryl, substituted heteroaryl, alkoxy, substituted alkoxy, halogen, nitro, cyano, hydroxy, —$NH_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino;
$R^1$ is selected from alkyl, substituted alkyl, aryl, substituted aryl, heteroaryl, substituted heteroaryl, alkoxy, substituted alkoxy, halogen, nitro, cyano, hydroxy, —$NH_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino;
each $R^{41}$ is independently selected from H, alkyl, substituted alkyl, aryl, substituted aryl, heteroaryl, substituted heteroaryl, alkoxy, substituted alkoxy, halogen, nitro, cyano, hydroxy, —$NH_2$, substituted amino, carboxy, sulfoxy, alkylsulfonyl, substituted alkylsulfonyl, alkanoyl, substituted alkanoyl, alkylsulfonamido, substituted alkylsulfonamido, alkylamido, substituted alkylamido, alkylamino and substituted alkylamino; and
n is 1-2;
or a salt thereof, or a solvate, hydrate or prodrug form thereof.

6. The method of claim 1, wherein A is a substituted heterocycle that is substituted with one or more groups selected from aryl, substituted aryl, carboxy, substituted carboxy, alkylsulfonyl, substituted alkylsulfonyl, alkanoyl, and substituted alkanoyl.

7. The method of claim 6, wherein A is a substituted heterocycle that is substituted with a substituted carboxy group.

8. The method of claim 7, wherein A has the formula:

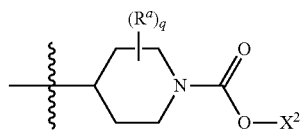

wherein:
each $R^a$ is independently selected from H, alkyl and substituted alkyl;
$X^2$ is selected from alkyl, substituted alkyl, aryl, substituted aryl, heterocycle, substituted heterocycle, heteroaryl, substituted heteroaryl, cycloalkyl, and substituted cycloalkyl;
q is 1-6.

9. The method of claim 5, wherein A is a substituted heterocycle that is substituted with one or more groups selected from aryl, substituted aryl, carboxy, substituted carboxy, alkylsulfonyl, substituted alkylsulfonyl, alkanoyl, and substituted alkanoyl.

10. The method of claim 9, wherein A is a substituted heterocycle that is substituted with a substituted carboxy group.

11. The method of claim 10, wherein A has the formula:

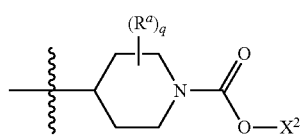

wherein:
each $R^a$ is independently selected from H, alkyl and substituted alkyl;
$X^2$ is selected from alkyl, substituted alkyl, aryl, substituted aryl, heterocycle, substituted heterocycle, heteroaryl, substituted heteroaryl, cycloalkyl, and substituted cycloalkyl;
q is 1-6.

12. The method of claim 1, wherein $Z^1$ is C ($CH_3$).
13. The method of claim 5, wherein $Z^1$ is C ($CH_3$).

* * * * *

UNITED STATES PATENT AND TRADEMARK OFFICE
CERTIFICATE OF CORRECTION

PATENT NO. : 12,180,220 B2
APPLICATION NO. : 17/484739
DATED : December 31, 2024
INVENTOR(S) : Solomon B. Ungashe et al.

It is certified that error appears in the above-identified patent and that said Letters Patent is hereby corrected as shown below:

In the Specification

Please replace "—SO2-alkyl, —SO2-aryl, SO2-heteroaryl," with -- —SO$_2$-alkyl, —SO$_2$-aryl, SO$_2$-heteroaryl, -- (Column 4, Lines 6-7).

Please replace "thiomorpholine-S,S-dioxide," with -- thiomorpholine-S, S-dioxide, -- (Column 7, Lines 60-61).

Please replace "$R^q$" with -- $R^a$ -- (Column 22, Line 64).

Please replace "aryl-$C_{1-4}$alkyl," with -- aryl-$C_{1-4}$ alkyl, -- (Column 29, Line 10).

Please replace "aryl-$C_{1-4}$alkyl," with -- aryl-$C_{1-4}$ alkyl, -- (Column 29, Line 11).

Please replace "formula" with -- formulae -- (Column 32, Line 1).

Please replace "$R^2$" with -- $R^1$ -- (Column 32, Line 3).

Please replace "$R^2$" with -- $R^1$ -- (Column 32, Line 3).

Please replace "$R^2$" with -- $R^1$ -- (Column 32, Line 4).

Please replace "$R^2$" with -- $R^1$ -- (Column 32, Line 4).

Please replace "formula" with -- formulae -- (Column 32, Line 5).

Please replace "formula" with -- formulae -- (Column 32, Line 10).

Please replace "formula" with -- formulae -- (Column 32, Line 14).

Signed and Sealed this
Sixth Day of May, 2025

Coke Morgan Stewart
*Acting Director of the United States Patent and Trademark Office*

Please replace "R$^a$" with -- R$^3$ -- (Column 47, Line 11).

Please replace "R$^a$" with -- R$^3$ -- (Column 47, Line 33).

Please replace "propanesulfonates," with -- propanesulfonate, -- (Column 66, Line 50).

Please replace "pentostatine," with -- pentostatin, -- (Column 75, Line 13).

Please replace "phenoxizone" with -- phenoxazone -- (Column 75, Line 24).

Please replace "navelbene," with -- navelbine, -- (Column 75, Line 30).

Please replace "reloxafine," with -- raloxifene, -- (Column 75, Line 31).

Please replace "ifosamide," with -- ifosfamide, -- (Column 75, Line 32).

Please replace "dolstatin" with -- dolastatin -- (Column 75, Line 37).

Please replace "cysterin," with -- cysteine, -- (Column 75, Line 40).

Please replace "pregestins," with -- progestins, -- (Column 75, Line 47).

Please replace "desoxyspergualin," with -- deoxyspergualin, -- (Column 75, Line 67).

Please replace "St" with -- St. -- (Column 76, Line 18).

Please replace "yannanensis)." with -- yunnanensis). -- (Column 76, Line 19).

Please replace "(Kaplift" with -- (Kaplitt -- (Column 78, Line 27).

Please replace "SW820" with -- SW620 -- (Column 78, Line 46).

Please replace "PenStrep" with -- Pen Strep -- (Column 78, Line 49).